(12) United States Patent
Wang et al.

(10) Patent No.: US 9,890,434 B2
(45) Date of Patent: Feb. 13, 2018

(54) METHOD FOR IDENTIFYING COMPOUND FOR INHIBITING AN ACTIVITY OF A HISTONE LYSINE DEMETHYLASE

(71) Applicant: NATIONAL TSING HUA UNIVERSITY, Hsinchu (TW)

(72) Inventors: Wen-Ching Wang, Hsinchu (TW); Hsing-Jien Kung, Miaoli County (TW); Chia-Han Chu, Taipei (TW); Jing-Moon Yang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 407 days.

(21) Appl. No.: 14/662,220

(22) Filed: Mar. 18, 2015

(65) Prior Publication Data

US 2015/0267241 A1    Sep. 24, 2015

Related U.S. Application Data

(60) Provisional application No. 61/955,225, filed on Mar. 19, 2014.

(51) Int. Cl.
 *C12Q 1/26* (2006.01)
 *C40B 30/02* (2006.01)
 *G06F 19/16* (2011.01)

(52) U.S. Cl.
 CPC ........ *C12Y 114/11027* (2013.01); *C12Q 1/26* (2013.01); *C40B 30/02* (2013.01); *G01N 2333/90245* (2013.01); *G01N 2500/04* (2013.01); *G06F 19/16* (2013.01)

(58) Field of Classification Search
 CPC .............. C12Y 114/11027; C12Q 1/26; G01N 2500/04; G01N 2333/90245; G06F 19/16; C40B 30/02
 See application file for complete search history.

*Primary Examiner* — Jeremy C Flinders
(74) *Attorney, Agent, or Firm* — Hannah M. Tien

(57) ABSTRACT

The present invention relates to a method for identifying a compound that inhibits an activity of a histone lysine demethylase.

11 Claims, 24 Drawing Sheets

SEQUENCE LISTING

<160> NUMBER OF SEQ ID NOS: 15

<210> SEQ ID NO 1
<211> LENGTH: 30
<212> TYPE: DNA
<213> ORGANISM: Homo sapiens
<220> FEATURE:
<221> NAME/KEY: primer_bind
<222> LOCATION: (1)..(30)
<223> OTHER INFORMATION: KDM4B forward

<400> SEQUENCE: 1
aaacatatgg ggtctgagga ccacggcgcc            30

<210> SEQ ID NO 2
<211> LENGTH: 33
<212> TYPE: DNA
<213> ORGANISM: Homo sapiens
<220> FEATURE:
<221> NAME/KEY: primer_bind
<222> LOCATION: (1)..(33)
<223> OTHER INFORMATION: KDM4B reverse

<400> SEQUENCE: 2
aaaaaactcg gggctctcga gctacgtggg ccg            33

```
<210> SEQ ID NO 3
<211> LENGTH: 30
<212> TYPE: DNA
<213> ORGANISM: Homo sapiens
<220> FEATURE:
<221> NAME/KEY: primer_bind
<222> LOCATION: (1)..(30)
<223> OTHER INFORMATION: KDM4A forward

<400> SEQUENCE: 3
aaacatatgg cgagcgaaag cgaaactctg                              30

<210> SEQ ID NO 4
<211> LENGTH: 30
<212> TYPE: DNA
<213> ORGANISM: Homo sapiens
<220> FEATURE:
<221> NAME/KEY: primer_bind
<222> LOCATION: (1)..(30)
<223> OTHER INFORMATION: KDM4A reverse

<400> SEQUENCE: 4
aaaggatccc tacgtgggca gagtatggtc                              30

<210> SEQ ID NO 5
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: KDM4A forward

<400> SEQUENCE: 5
aggagagtga actgcctcca                                         20

<210> SEQ ID NO 6
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: KDM4A reverse

<400> SEQUENCE: 6
ggtctccttc ctctccatcc                                         20

<210> SEQ ID NO 7
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: KDM4B forward

<400> SEQUENCE: 7
tcacgcagta caatatccag                                         20

<210> SEQ ID NO 8
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: KDM4B reverse
```

-continued

```
<400> SEQUENCE: 8
tcgtcatcat acaaagagcc                                                 20

<210> SEQ ID NO 9
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: actin forward

<400> SEQUENCE: 9
gtaccactgg catcgtgatg gact                                            24

<210> SEQ ID NO 10
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: actin reverse

<400> SEQUENCE: 10
ccgctcattg ccaatggtga t                                               21

<210> SEQ ID NO 11
<211> LENGTH: 1096
<212> TYPE: PRT
<213> ORGANISM: Homo sapiens
<220> FEATURE:
<221> NAME/KEY: PEPTIDE
<222> LOCATION: (1)..(1096)
<223> OTHER INFORMATION: KDM4B

<400> SEQUENCE: 11
```

Met Gly Ser Glu Asp His Gly Ala Gln Asn Pro Ser Cys Lys Ile Met
1               5                   10                  15

Thr Phe Arg Pro Thr Met Glu Glu Phe Lys Asp Phe Asn Lys Tyr Val
            20                  25                  30

Ala Tyr Ile Glu Ser Gln Gly Ala His Arg Ala Gly Leu Ala Lys Ile
        35                  40                  45

Ile Pro Pro Lys Glu Trp Lys Pro Arg Gln Thr Tyr Asp Asp Ile Asp
    50                  55                  60

Asp Val Val Ile Pro Ala Pro Ile Gln Gln Val Val Thr Gly Gln Ser
65                  70                  75                  80

Gly Leu Phe Thr Gln Tyr Asn Ile Gln Lys Lys Ala Met Thr Val Gly
                85                  90                  95

Glu Tyr Arg Arg Leu Ala Asn Ser Glu Lys Tyr Cys Thr Pro Arg His
            100                 105                 110

Gln Asp Phe Asp Asp Leu Glu Arg Lys Tyr Trp Lys Asn Leu Thr Phe
        115                 120                 125

Val Ser Pro Ile Tyr Gly Ala Asp Ile Ser Gly Ser Leu Tyr Asp Asp
    130                 135                 140

Asp Val Ala Gln Trp Asn Ile Gly Ser Leu Arg Thr Ile Leu Asp Met
145                 150                 155                 160

Val Glu Arg Glu Cys Gly Thr Ile Ile Glu Gly Val Asn Thr Pro Tyr
                165                 170                 175

Leu Tyr Phe Gly Met Trp Lys Thr Thr Phe Ala Trp His Thr Glu Asp
            180                 185                 190

```
Met Asp Leu Tyr Ser Ile Asn Tyr Leu His Phe Gly Glu Pro Lys Ser
            195                 200                 205

Trp Tyr Ala Ile Pro Pro Glu His Gly Lys Arg Leu Glu Arg Leu Ala
        210                 215                 220

Ile Gly Phe Phe Pro Gly Ser Ser Gln Gly Cys Asp Ala Phe Leu Arg
225                 230                 235                 240

His Lys Met Thr Leu Ile Ser Pro Ile Leu Lys Lys Tyr Gly Ile
            245                 250                 255

Pro Phe Ser Arg Ile Thr Gln Glu Ala Gly Glu Phe Met Ile Thr Phe
            260                 265                 270

Pro Tyr Gly Tyr His Ala Gly Phe Asn His Gly Phe Asn Cys Ala Glu
            275                 280                 285

Ser Thr Asn Phe Ala Thr Leu Arg Trp Ile Asp Tyr Gly Lys Val Ala
        290                 295                 300

Thr Gln Cys Thr Cys Arg Lys Asp Met Val Lys Ile Ser Met Asp Val
305                 310                 315                 320

Phe Val Arg Ile Leu Gln Pro Glu Arg Tyr Glu Leu Trp Lys Gln Gly
                325                 330                 335

Lys Asp Leu Thr Val Leu Asp His Thr Arg Pro Thr Ala Leu Thr Ser
            340                 345                 350

Pro Glu Leu Ser Ser Trp Ser Ala Ser Arg Ala Ser Leu Lys Ala Lys
            355                 360                 365

Leu Leu Arg Arg Ser His Arg Lys Arg Ser Gln Pro Lys Lys Pro Lys
            370                 375                 380

Pro Glu Asp Pro Lys Phe Pro Gly Glu Gly Thr Ala Gly Ala Ala Leu
385                 390                 395                 400

Leu Glu Glu Ala Gly Gly Ser Val Lys Glu Ala Gly Pro Glu Val
                405                 410                 415

Asp Pro Glu Glu Glu Glu Glu Pro Gln Pro Leu His Gly Arg
            420                 425                 430

Glu Ala Glu Gly Ala Glu Glu Asp Gly Arg Gly Lys Leu Arg Pro Thr
            435                 440                 445

Lys Ala Lys Ser Glu Arg Lys Lys Ser Phe Gly Leu Leu Pro Pro
        450                 455                 460

Gln Leu Pro Pro Pro Ala His Phe Pro Ser Glu Glu Ala Leu Trp
465                 470                 475                 480

Leu Pro Ser Pro Leu Glu Pro Val Leu Gly Pro Gly Pro Ala Ala
            485                 490                 495

Met Glu Glu Ser Pro Leu Pro Ala Pro Leu Asn Val Val Pro Pro Glu
            500                 505                 510

Val Pro Ser Glu Glu Leu Glu Ala Lys Pro Arg Pro Ile Ile Pro Met
        515                 520                 525

Leu Tyr Val Val Pro Arg Pro Gly Lys Ala Ala Phe Asn Gln Glu His
        530                 535                 540

Val Ser Cys Gln Gln Ala Phe Glu His Phe Ala Gln Lys Gly Pro Thr
545                 550                 555                 560

Trp Lys Glu Pro Val Ser Pro Met Glu Leu Thr Gly Pro Glu Asp Gly
                565                 570                 575

Ala Ala Ser Ser Gly Ala Gly Arg Met Glu Thr Lys Ala Arg Ala Gly
            580                 585                 590

Glu Gly Gln Ala Pro Ser Thr Phe Ser Lys Leu Lys Met Glu Ile Lys
            595                 600                 605
```

```
Lys Ser Arg Arg His Pro Leu Gly Arg Pro Pro Thr Arg Ser Pro Leu
610                 615                 620

Ser Val Val Lys Gln Glu Ala Ser Ser Asp Glu Glu Ala Ser Pro Phe
625                 630                 635                 640

Ser Gly Glu Glu Asp Val Ser Asp Pro Asp Ala Leu Arg Pro Leu Leu
                645                 650                 655

Ser Leu Gln Trp Lys Asn Arg Ala Ala Ser Phe Gln Ala Glu Arg Lys
                660                 665                 670

Phe Asn Ala Ala Ala Arg Thr Glu Pro Tyr Cys Ala Ile Cys Thr
                675                 680                 685

Leu Phe Tyr Pro Tyr Cys Gln Ala Leu Gln Thr Glu Lys Glu Ala Pro
690                 695                 700

Ile Ala Ser Leu Gly Lys Gly Cys Pro Ala Thr Leu Pro Ser Lys Ser
705                 710                 715                 720

Arg Gln Lys Thr Arg Pro Leu Ile Pro Glu Met Cys Phe Thr Ser Gly
                725                 730                 735

Gly Glu Asn Thr Glu Pro Leu Pro Ala Asn Ser Tyr Ile Gly Asp Asp
                740                 745                 750

Gly Thr Ser Pro Leu Ile Ala Cys Gly Lys Cys Cys Leu Gln Val His
                755                 760                 765

Ala Ser Cys Tyr Gly Ile Arg Pro Glu Leu Val Asn Glu Gly Trp Thr
770                 775                 780

Cys Ser Arg Cys Ala Ala His Ala Trp Thr Ala Glu Cys Cys Leu Cys
785                 790                 795                 800

Asn Leu Arg Gly Gly Ala Leu Gln Met Thr Thr Asp Arg Arg Trp Ile
                805                 810                 815

His Val Ile Cys Ala Ile Ala Val Pro Glu Ala Arg Phe Leu Asn Val
                820                 825                 830

Ile Glu Arg His Pro Val Asp Ile Ser Ala Ile Pro Glu Gln Arg Trp
                835                 840                 845

Lys Leu Lys Cys Val Tyr Cys Arg Lys Arg Met Lys Lys Val Ser Gly
850                 855                 860

Ala Cys Ile Gln Cys Ser Tyr Glu His Cys Ser Thr Ser Phe His Val
865                 870                 875                 880

Thr Cys Ala His Ala Ala Gly Val Leu Met Glu Pro Asp Asp Trp Pro
                885                 890                 895

Tyr Val Val Ser Ile Thr Cys Leu Lys His Lys Ser Gly Gly His Ala
                900                 905                 910

Val Gln Leu Leu Arg Ala Val Ser Leu Gly Gln Val Val Ile Thr Lys
                915                 920                 925

Asn Arg Asn Gly Leu Tyr Tyr Arg Cys Arg Val Ile Gly Ala Ala Ser
930                 935                 940

Gln Thr Cys Tyr Glu Val Asn Phe Asp Asp Gly Ser Tyr Ser Asp Asn
945                 950                 955                 960

Leu Tyr Pro Glu Ser Ile Thr Ser Arg Asp Cys Val Gln Leu Gly Pro
                965                 970                 975

Pro Ser Glu Gly Glu Leu Val Glu Leu Arg Trp Thr Asp Gly Asn Leu
                980                 985                 990

Tyr Lys Ala Lys Phe Ile Ser  Val Thr Ser His Ile Tyr Gln Val
                995                 1000                1005

Glu Phe Glu Asp Gly Ser Gln  Leu Thr Val Lys Arg  Gly Asp Ile
                1010                1015                1020

Phe Thr  Leu Glu Glu Glu Leu  Pro Lys Arg Val Arg  Ser Arg Leu
```

-continued

```
           1025                1030                1035

Ser Leu Ser Thr Gly Ala Pro  Gln Glu Pro Ala Phe  Ser Gly Glu
        1040                1045                1050

Glu Ala Lys Ala Ala Lys Arg  Pro Arg Val Gly Thr  Pro Leu Ala
    1055                1060                1065

Thr Glu Asp Ser Gly Arg Ser  Gln Asp Tyr Val Ala  Phe Val Glu
        1070                1075                1080

Ser Leu Leu Gln Val Gln Gly  Arg Pro Gly Ala Pro  Phe
        1085                1090                1095

<210> SEQ ID NO 12
<211> LENGTH: 1064
<212> TYPE: PRT
<213> ORGANISM: Homo sapiens
<220> FEATURE:
<221> NAME/KEY: PEPTIDE
<222> LOCATION: (1)..(1064)
<223> OTHER INFORMATION: KDM4A

<400> SEQUENCE: 12

Met Ala Ser Glu Ser Glu Thr  Leu Asn Pro Ser Ala  Arg Ile Met Thr
1               5                   10                  15

Phe Tyr Pro Thr Met Glu Glu  Phe Arg Asn Phe Ser  Arg Tyr Ile Ala
            20                  25                  30

Tyr Ile Glu Ser Gln Gly Ala  His Arg Ala Gly Leu  Ala Lys Val Val
        35                  40                  45

Pro Pro Lys Glu Trp Lys Pro  Arg Ala Ser Tyr Asp  Asp Ile Asp Asp
    50                  55                  60

Leu Val Ile Pro Ala Pro Ile  Gln Gln Leu Val Thr  Gly Gln Ser Gly
65              70                  75                  80

Leu Phe Thr Gln Tyr Asn Ile  Gln Lys Lys Ala Met  Thr Val Arg Glu
            85                  90                  95

Phe Arg Lys Ile Ala Asn Ser  Asp Lys Tyr Cys Thr  Pro Arg Tyr Ser
            100                 105                 110

Glu Phe Glu Glu Leu Glu Arg  Lys Tyr Trp Lys Asn  Leu Thr Phe Asn
        115                 120                 125

Pro Pro Ile Tyr Gly Ala Asp  Val Asn Gly Thr Leu  Tyr Glu Lys His
    130                 135                 140

Val Asp Glu Trp Asn Ile Gly  Arg Leu Arg Thr Ile  Leu Asp Leu Val
145             150                 155                 160

Glu Lys Glu Ser Gly Ile Thr  Ile Glu Gly Val Asn  Thr Pro Tyr Leu
            165                 170                 175

Tyr Phe Gly Met Trp Lys Thr  Ser Phe Ala Trp His  Thr Glu Asp Met
            180                 185                 190

Asp Leu Tyr Ser Ile Asn Tyr  Leu His Phe Gly Glu  Pro Lys Ser Trp
        195                 200                 205

Tyr Ser Val Pro Pro Glu His  Gly Lys Arg Leu Glu  Arg Leu Ala Lys
    210                 215                 220

Gly Phe Phe Pro Gly Ser Ala  Gln Ser Cys Glu Ala  Phe Leu Arg His
225             230                 235                 240

Lys Met Thr Leu Ile Ser Pro  Leu Met Leu Lys Lys  Tyr Gly Ile Pro
            245                 250                 255

Phe Asp Lys Val Thr Gln Glu  Ala Gly Glu Phe Met  Ile Thr Phe Pro
            260                 265                 270

Tyr Gly Tyr His Ala Gly Phe  Asn His Gly Phe Asn  Cys Ala Glu Ser
        275                 280                 285
```

-continued

Thr Asn Phe Ala Thr Arg Arg Trp Ile Glu Tyr Gly Lys Gln Ala Val
                290                 295                 300

Leu Cys Ser Cys Arg Lys Asp Met Val Lys Ile Ser Met Asp Val Phe
305                 310                 315                 320

Val Arg Lys Phe Gln Pro Glu Arg Tyr Lys Leu Trp Lys Ala Gly Lys
                325                 330                 335

Asp Asn Thr Val Ile Asp His Thr Leu Pro Thr Pro Glu Ala Ala Glu
                340                 345                 350

Phe Leu Lys Glu Ser Glu Leu Pro Arg Ala Gly Asn Glu Glu Glu
                355                 360                 365

Cys Pro Glu Glu Asp Met Glu Gly Val Glu Asp Gly Glu Glu Gly Asp
                370                 375                 380

Leu Lys Thr Ser Leu Ala Lys His Arg Ile Gly Thr Lys Arg His Arg
385                 390                 395                 400

Val Cys Leu Glu Ile Pro Gln Glu Val Ser Gln Ser Glu Leu Phe Pro
                405                 410                 415

Lys Glu Asp Leu Ser Ser Glu Gln Tyr Glu Met Thr Glu Cys Pro Ala
                420                 425                 430

Ala Leu Ala Pro Val Arg Pro Thr His Ser Ser Val Arg Gln Val Glu
                435                 440                 445

Asp Gly Leu Thr Phe Pro Asp Tyr Ser Asp Ser Thr Glu Val Lys Phe
                450                 455                 460

Glu Glu Leu Lys Asn Val Lys Leu Glu Glu Glu Asp Glu Glu Glu Glu
465                 470                 475                 480

Gln Ala Ala Ala Leu Asp Leu Ser Val Asn Pro Ala Ser Val Gly
                485                 490                 495

Gly Arg Leu Val Phe Ser Gly Ser Lys Lys Lys Ser Ser Ser Ser Leu
                500                 505                 510

Gly Ser Gly Ser Ser Arg Asp Ser Ile Ser Ser Asp Ser Glu Thr Ser
                515                 520                 525

Glu Pro Leu Ser Cys Arg Ala Gln Gly Gln Thr Gly Val Leu Thr Val
530                 535                 540

His Ser Tyr Ala Lys Gly Asp Gly Arg Val Thr Val Gly Glu Pro Cys
545                 550                 555                 560

Thr Arg Lys Lys Gly Ser Ala Ala Arg Ser Phe Ser Glu Arg Glu Leu
                565                 570                 575

Ala Glu Val Ala Asp Glu Tyr Met Phe Ser Leu Glu Glu Asn Lys Lys
                580                 585                 590

Ser Lys Gly Arg Arg Gln Pro Leu Ser Lys Leu Pro Arg His His Pro
                595                 600                 605

Leu Val Leu Gln Glu Cys Val Ser Asp Asp Glu Thr Ser Glu Gln Leu
                610                 615                 620

Thr Pro Glu Glu Glu Ala Glu Glu Thr Glu Ala Trp Ala Lys Pro Leu
625                 630                 635                 640

Ser Gln Leu Trp Gln Asn Arg Pro Pro Asn Phe Glu Ala Glu Lys Glu
                645                 650                 655

Phe Asn Glu Thr Met Ala Gln Gln Ala Pro His Cys Ala Val Cys Met
                660                 665                 670

Ile Phe Gln Thr Tyr His Gln Val Glu Phe Gly Gly Phe Asn Gln Asn
                675                 680                 685

Cys Gly Asn Ala Ser Asp Leu Ala Pro Gln Lys Gln Arg Thr Lys Pro
                690                 695                 700

```
Leu Ile Pro Glu Met Cys Phe Thr Ser Thr Gly Cys Ser Thr Asp Ile
705                 710                 715                 720

Asn Leu Ser Thr Pro Tyr Leu Glu Glu Asp Gly Thr Ser Ile Leu Val
            725                 730                 735

Ser Cys Lys Lys Cys Ser Val Arg Val His Ala Ser Cys Tyr Gly Val
            740                 745                 750

Pro Pro Ala Lys Ala Ser Glu Asp Trp Met Cys Ser Arg Cys Ser Ala
            755                 760                 765

Asn Ala Leu Glu Glu Asp Cys Cys Leu Cys Ser Leu Arg Gly Gly Ala
770                 775                 780

Leu Gln Arg Ala Asn Asp Asp Arg Trp Val His Val Ser Cys Ala Val
785                 790                 795                 800

Ala Ile Leu Glu Ala Arg Phe Val Asn Ile Ala Glu Arg Ser Pro Val
            805                 810                 815

Asp Val Ser Lys Ile Pro Leu Pro Arg Phe Lys Leu Lys Cys Ile Phe
            820                 825                 830

Cys Lys Lys Arg Arg Lys Arg Thr Ala Gly Cys Cys Val Gln Cys Ser
            835                 840                 845

His Gly Arg Cys Pro Thr Ala Phe His Val Ser Cys Ala Gln Ala Ala
            850                 855                 860

Gly Val Met Met Gln Pro Asp Asp Trp Pro Phe Val Val Phe Ile Thr
865                 870                 875                 880

Cys Phe Arg His Lys Ile Pro Asn Leu Glu Arg Ala Lys Gly Ala Leu
            885                 890                 895

Gln Ser Ile Thr Ala Gly Gln Lys Val Ile Ser Lys His Lys Asn Gly
            900                 905                 910

Arg Phe Tyr Gln Cys Glu Val Val Arg Leu Thr Thr Glu Thr Phe Tyr
            915                 920                 925

Glu Val Asn Phe Asp Asp Gly Ser Phe Ser Asp Asn Leu Tyr Pro Glu
            930                 935                 940

Asp Ile Val Ser Gln Asp Cys Leu Gln Phe Gly Pro Pro Ala Glu Gly
945                 950                 955                 960

Glu Val Val Gln Val Arg Trp Thr Asp Gly Gln Val Tyr Gly Ala Lys
            965                 970                 975

Phe Val Ala Ser His Pro Ile Gln Met Tyr Gln Val Glu Phe Glu Asp
            980                 985                 990

Gly Ser Gln Leu Val Val Lys Arg Asp Asp Val Tyr Thr Leu Asp Glu
            995                 1000                1005

Glu Leu Pro Lys Arg Val Lys Ser Arg Leu Ser Val Ala Ser Asp
    1010                1015                1020

Met Arg Phe Asn Glu Ile Phe Thr Glu Lys Glu Val Lys Gln Glu
    1025                1030                1035

Lys Lys Arg Gln Arg Val Ile Asn Ser Arg Tyr Arg Glu Asp Tyr
    1040                1045                1050

Ile Glu Pro Ala Leu Tyr Arg Ala Ile Met Glu
    1055                1060

<210> SEQ ID NO 13
<211> LENGTH: 1056
<212> TYPE: PRT
<213> ORGANISM: Homo sapiens
<220> FEATURE:
<221> NAME/KEY: PEPTIDE
<222> LOCATION: (1)..(1056)
<223> OTHER INFORMATION: KDM4C
```

<400> SEQUENCE: 13

```
Met Glu Val Ala Glu Val Glu Ser Pro Leu Asn Pro Ser Cys Lys Ile
1               5                   10                  15

Met Thr Phe Arg Pro Ser Met Glu Glu Phe Arg Glu Phe Asn Lys Tyr
            20                  25                  30

Leu Ala Tyr Met Glu Ser Lys Gly Ala His Arg Ala Gly Leu Ala Lys
        35                  40                  45

Val Ile Pro Pro Lys Glu Trp Lys Pro Arg Gln Cys Tyr Asp Asp Ile
50                  55                  60

Asp Asn Leu Leu Ile Pro Ala Pro Ile Gln Gln Met Val Thr Gly Gln
65                  70                  75                  80

Ser Gly Leu Phe Thr Gln Tyr Asn Ile Gln Lys Lys Ala Met Thr Val
                85                  90                  95

Lys Glu Phe Arg Gln Leu Ala Asn Ser Gly Lys Tyr Cys Thr Pro Arg
            100                 105                 110

Tyr Leu Asp Tyr Glu Asp Leu Glu Arg Lys Tyr Trp Lys Asn Leu Thr
        115                 120                 125

Phe Val Ala Pro Ile Tyr Gly Ala Asp Ile Asn Gly Ser Ile Tyr Asp
130                 135                 140

Glu Gly Val Asp Glu Trp Asn Ile Ala Arg Leu Asn Thr Val Leu Asp
145                 150                 155                 160

Val Val Glu Glu Glu Cys Gly Ile Ser Ile Glu Gly Val Asn Thr Pro
                165                 170                 175

Tyr Leu Tyr Phe Gly Met Trp Lys Thr Thr Phe Ala Trp His Thr Glu
            180                 185                 190

Asp Met Asp Leu Tyr Ser Ile Asn Tyr Leu His Phe Gly Glu Pro Lys
        195                 200                 205

Ser Trp Tyr Ala Ile Pro Pro Glu His Gly Lys Arg Leu Glu Arg Leu
210                 215                 220

Ala Gln Gly Phe Phe Pro Ser Ser Gln Gly Cys Asp Ala Phe Leu
225                 230                 235                 240

Arg His Lys Met Thr Leu Ile Ser Pro Ser Val Leu Lys Lys Tyr Gly
                245                 250                 255

Ile Pro Phe Asp Lys Ile Thr Gln Glu Ala Gly Glu Phe Met Ile Thr
            260                 265                 270

Phe Pro Tyr Gly Tyr His Ala Gly Phe Asn His Gly Phe Asn Cys Ala
        275                 280                 285

Glu Ser Thr Asn Phe Ala Thr Val Arg Trp Ile Asp Tyr Gly Lys Val
290                 295                 300

Ala Lys Leu Cys Thr Cys Arg Lys Asp Met Val Lys Ile Ser Met Asp
305                 310                 315                 320

Ile Phe Val Arg Lys Phe Gln Pro Asp Arg Tyr Gln Leu Trp Lys Gln
                325                 330                 335

Gly Lys Asp Ile Tyr Thr Ile Asp His Thr Lys Pro Thr Pro Ala Ser
            340                 345                 350

Thr Pro Glu Val Lys Ala Trp Leu Gln Arg Arg Lys Val Arg Lys
        355                 360                 365

Ala Ser Arg Ser Phe Gln Cys Ala Arg Ser Thr Ser Lys Arg Pro Lys
370                 375                 380

Ala Asp Glu Glu Glu Glu Val Ser Asp Glu Val Asp Gly Ala Glu Val
385                 390                 395                 400

Pro Asn Pro Asp Ser Val Thr Asp Leu Lys Val Ser Glu Lys Ser
                405                 410                 415
```

-continued

Glu Ala Ala Val Lys Leu Arg Asn Thr Glu Ala Ser Ser Glu Glu Glu
        420                 425             430

Ser Ser Ala Ser Arg Met Gln Val Glu Gln Asn Leu Ser Asp His Ile
        435                 440             445

Lys Leu Ser Gly Asn Ser Cys Leu Ser Thr Ser Val Thr Glu Asp Ile
450                 455                 460

Lys Thr Glu Asp Asp Lys Ala Tyr Ala Tyr Arg Ser Val Pro Ser Ile
465             470                 475                 480

Ser Ser Glu Ala Asp Asp Ser Ile Pro Leu Ser Ser Gly Tyr Glu Lys
                485                 490                 495

Pro Glu Lys Ser Asp Pro Ser Glu Leu Ser Trp Pro Lys Ser Pro Glu
            500                 505                 510

Ser Cys Ser Ser Val Ala Glu Ser Asn Gly Val Leu Thr Glu Gly Glu
            515                 520                 525

Glu Ser Asp Val Glu Ser His Gly Asn Gly Leu Glu Pro Gly Glu Ile
        530                 535                 540

Pro Ala Val Pro Ser Gly Glu Arg Asn Ser Phe Lys Val Pro Ser Ile
545                 550                 555                 560

Ala Glu Gly Glu Asn Lys Thr Ser Lys Ser Trp Arg His Pro Leu Ser
                565                 570                 575

Arg Pro Pro Ala Arg Ser Pro Met Thr Leu Val Lys Gln Gln Ala Pro
            580                 585                 590

Ser Asp Glu Glu Leu Pro Glu Val Leu Ser Ile Glu Glu Glu Val Glu
        595                 600                 605

Glu Thr Glu Ser Trp Ala Lys Pro Leu Ile His Leu Trp Gln Thr Lys
        610                 615                 620

Ser Pro Asn Phe Ala Ala Glu Gln Glu Tyr Asn Ala Thr Val Ala Arg
625                 630                 635                 640

Met Lys Pro His Cys Ala Ile Cys Thr Leu Leu Met Pro Tyr His Lys
                645                 650                 655

Pro Asp Ser Ser Asn Glu Glu Asn Asp Ala Arg Trp Glu Thr Lys Leu
            660                 665                 670

Asp Glu Val Val Thr Ser Glu Gly Lys Thr Lys Pro Leu Ile Pro Glu
        675                 680                 685

Met Cys Phe Ile Tyr Ser Glu Glu Asn Ile Glu Tyr Ser Pro Pro Asn
        690                 695                 700

Ala Phe Leu Glu Glu Asp Gly Thr Ser Leu Leu Ile Ser Cys Ala Lys
705                 710                 715                 720

Cys Cys Val Arg Val His Ala Ser Cys Tyr Gly Ile Pro Ser His Glu
                725                 730                 735

Ile Cys Asp Gly Trp Leu Cys Ala Arg Cys Lys Arg Asn Ala Trp Thr
            740                 745                 750

Ala Glu Cys Cys Leu Cys Asn Leu Arg Gly Gly Ala Leu Lys Gln Thr
            755                 760                 765

Lys Asn Asn Lys Trp Ala His Val Met Cys Ala Val Ala Val Pro Glu
        770                 775                 780

Val Arg Phe Thr Asn Val Pro Glu Arg Thr Gln Ile Asp Val Gly Arg
785                 790                 795                 800

Ile Pro Leu Gln Arg Leu Lys Leu Lys Cys Ile Phe Cys Arg His Arg
                805                 810                 815

Val Lys Arg Val Ser Gly Ala Cys Ile Gln Cys Ser Tyr Gly Arg Cys
            820                 825                 830

-continued

```
Pro Ala Ser Phe His Val Thr Cys Ala His Ala Ala Gly Val Leu Met
            835                 840                 845

Glu Pro Asp Asp Trp Pro Tyr Val Val Asn Ile Thr Cys Phe Arg His
850                 855                 860

Lys Val Asn Pro Asn Val Lys Ser Lys Ala Cys Glu Lys Val Ile Ser
865                 870                 875                 880

Val Gly Gln Thr Val Ile Thr Lys His Arg Asn Thr Arg Tyr Tyr Ser
                885                 890                 895

Cys Arg Val Met Ala Val Thr Ser Gln Thr Phe Tyr Glu Val Met Phe
            900                 905                 910

Asp Asp Gly Ser Phe Ser Arg Asp Thr Phe Pro Glu Asp Ile Val Ser
            915                 920                 925

Arg Asp Cys Leu Lys Leu Gly Pro Ala Glu Gly Glu Val Val Gln
            930                 935                 940

Val Lys Trp Pro Asp Gly Lys Leu Tyr Gly Ala Lys Tyr Phe Gly Ser
945                 950                 955                 960

Asn Ile Ala His Met Tyr Gln Val Glu Phe Gly Asp Gly Ser Gln Ile
                965                 970                 975

Ala Met Lys Arg Glu Asp Ile Tyr Thr Leu Asp Glu Glu Leu Pro Lys
            980                 985                 990

Arg Val Lys Ala Arg Phe Ser Thr Ala Ser Asp Met Arg Phe Glu Asp
            995                 1000                1005

Thr Phe Tyr Gly Ala Asp Ile Ile Gln Gly Glu Arg Lys Arg Gln
    1010                1015                1020

Arg Val Leu Ser Ser Arg Phe Lys Asn Glu Tyr Val Ala Asp Pro
    1025                1030                1035

Val Tyr Arg Thr Phe Leu Lys Ser Ser Phe Gln Lys Lys Cys Gln
    1040                1045                1050

Lys Arg Gln
    1055

<210> SEQ ID NO 14
<211> LENGTH: 523
<212> TYPE: PRT
<213> ORGANISM: Homo sapiens
<220> FEATURE:
<221> NAME/KEY: PEPTIDE
<222> LOCATION: (1)..(523)
<223> OTHER INFORMATION: KDM4D

<400> SEQUENCE: 14

Met Glu Thr Met Lys Ser Lys Ala Asn Cys Ala Gln Asn Pro Asn Cys
1               5                   10                  15

Asn Ile Met Ile Phe His Pro Thr Lys Glu Glu Phe Asn Asp Phe Asp
            20                  25                  30

Lys Tyr Ile Ala Tyr Met Glu Ser Gln Gly Ala His Arg Ala Gly Leu
        35                  40                  45

Ala Lys Ile Ile Pro Pro Lys Glu Trp Lys Ala Arg Glu Thr Tyr Asp
    50                  55                  60

Asn Ile Ser Glu Ile Leu Ile Ala Thr Pro Leu Gln Gln Val Ala Ser
65                  70                  75                  80

Gly Arg Ala Gly Val Phe Thr Gln Tyr His Lys Lys Lys Lys Ala Met
                85                  90                  95

Thr Val Gly Glu Tyr Arg His Leu Ala Asn Ser Lys Lys Tyr Gln Thr
            100                 105                 110

Pro Pro His Gln Asn Phe Glu Asp Leu Glu Arg Lys Tyr Trp Lys Asn
```

```
            115                 120                 125
Arg Ile Tyr Asn Ser Pro Ile Tyr Gly Ala Asp Ile Ser Gly Ser Leu
    130                 135                 140

Phe Asp Glu Asn Thr Lys Gln Trp Asn Leu Gly His Leu Gly Thr Ile
145                 150                 155                 160

Gln Asp Leu Leu Glu Lys Cys Gly Val Val Ile Glu Gly Val Asn
                165                 170                 175

Thr Pro Tyr Leu Tyr Phe Gly Met Trp Lys Thr Thr Phe Ala Trp His
        180                 185                 190

Thr Glu Asp Met Asp Leu Tyr Ser Ile Asn Tyr Leu His Leu Gly Glu
            195                 200                 205

Pro Lys Thr Trp Tyr Val Val Pro Pro Glu His Gly Gln Arg Leu Glu
        210                 215                 220

Arg Leu Ala Arg Glu Leu Phe Pro Gly Ser Ser Arg Gly Cys Gly Ala
225                 230                 235                 240

Phe Leu Arg His Lys Val Ala Leu Ile Ser Pro Thr Val Leu Lys Glu
                245                 250                 255

Asn Gly Ile Pro Phe Asn Arg Ile Thr Gln Glu Ala Gly Glu Phe Met
            260                 265                 270

Val Thr Phe Pro Tyr Gly Tyr His Ala Gly Phe Asn His Gly Phe Asn
        275                 280                 285

Cys Ala Glu Ala Ile Asn Phe Ala Thr Pro Arg Trp Ile Asp Tyr Gly
290                 295                 300

Lys Met Ala Ser Gln Cys Ser Cys Gly Glu Ala Arg Val Thr Phe Ser
305                 310                 315                 320

Met Asp Ala Phe Val Arg Ile Leu Gln Pro Glu Arg Tyr Asp Leu Trp
                325                 330                 335

Lys Arg Gly Gln Asp Arg Ala Val Val Asp His Met Glu Pro Arg Val
            340                 345                 350

Pro Ala Ser Gln Glu Leu Ser Thr Gln Lys Glu Val Gln Leu Pro Arg
        355                 360                 365

Arg Ala Ala Leu Gly Leu Arg Gln Leu Pro Ser His Trp Ala Arg His
370                 375                 380

Ser Pro Trp Pro Met Ala Ala Arg Ser Gly Thr Arg Cys His Thr Leu
385                 390                 395                 400

Val Cys Ser Ser Leu Pro Arg Arg Ser Ala Val Ser Gly Thr Ala Thr
                405                 410                 415

Gln Pro Arg Ala Ala Val His Ser Ser Lys Lys Pro Ser Ser Thr
            420                 425                 430

Pro Ser Ser Thr Pro Gly Pro Ser Ala Gln Ile Ile His Pro Ser Asn
        435                 440                 445

Gly Arg Arg Gly Arg Gly Arg Pro Pro Gln Lys Leu Arg Ala Gln Glu
            450                 455                 460

Leu Thr Leu Gln Thr Pro Ala Lys Arg Pro Leu Leu Ala Gly Thr Thr
465                 470                 475                 480

Cys Thr Ala Ser Gly Pro Glu Pro Glu Pro Leu Pro Glu Asp Gly Ala
                485                 490                 495

Leu Met Asp Lys Pro Val Pro Leu Ser Pro Gly Leu Gln His Pro Val
            500                 505                 510

Lys Ala Ser Gly Cys Ser Trp Ala Pro Val Pro
        515                 520

<210> SEQ ID NO 15
```

```
<211> LENGTH: 506
<212> TYPE: PRT
<213> ORGANISM: Homo sapiens
<220> FEATURE:
<221> NAME/KEY: PEPTIDE
<222> LOCATION: (1)..(506)
<223> OTHER INFORMATION: KDM4E

<400> SEQUENCE: 15
```

| | | | | | | | | | | | | | | |
|---|---|---|---|---|---|---|---|---|---|---|---|---|---|---|
| Met | Lys | Ser | Val | His | Ser | Ser | Pro | Gln | Asn | Thr | Ser | His | Thr | Ile | Met |
| 1 | | | | 5 | | | | | 10 | | | | | 15 | |
| Thr | Phe | Tyr | Pro | Thr | Met | Glu | Glu | Phe | Ala | Asp | Phe | Asn | Thr | Tyr | Val |
| | | | 20 | | | | | 25 | | | | | 30 | | |
| Ala | Tyr | Met | Glu | Ser | Gln | Gly | Ala | His | Gln | Ala | Gly | Leu | Ala | Lys | Val |
| | | | 35 | | | | | 40 | | | | | 45 | | |
| Ile | Pro | Pro | Lys | Glu | Trp | Lys | Ala | Arg | Gln | Met | Tyr | Asp | Asp | Ile | Glu |
| | 50 | | | | | 55 | | | | | 60 | | | | |
| Asp | Ile | Leu | Ile | Ala | Thr | Pro | Leu | Gln | Gln | Val | Thr | Ser | Gly | Gln | Gly |
| 65 | | | | | 70 | | | | | 75 | | | | | 80 |
| Gly | Val | Phe | Thr | Gln | Tyr | His | Lys | Lys | Lys | Lys | Ala | Met | Arg | Val | Gly |
| | | | | 85 | | | | | 90 | | | | | 95 | |
| Gln | Tyr | Arg | Arg | Leu | Ala | Asn | Ser | Lys | Lys | Tyr | Gln | Thr | Pro | Pro | His |
| | | | 100 | | | | | 105 | | | | | 110 | | |
| Gln | Asn | Phe | Ala | Asp | Leu | Glu | Gln | Arg | Tyr | Trp | Lys | Ser | His | Pro | Gly |
| | | | 115 | | | | | 120 | | | | | 125 | | |
| Asn | Pro | Pro | Ile | Tyr | Gly | Ala | Asp | Ile | Ser | Gly | Ser | Leu | Phe | Glu | Glu |
| | 130 | | | | | 135 | | | | | 140 | | | | |
| Ser | Thr | Lys | Gln | Trp | Asn | Leu | Gly | His | Leu | Gly | Thr | Ile | Leu | Asp | Leu |
| 145 | | | | | 150 | | | | | 155 | | | | | 160 |
| Leu | Glu | Gln | Glu | Cys | Gly | Val | Val | Ile | Glu | Gly | Val | Asn | Thr | Pro | Tyr |
| | | | | 165 | | | | | 170 | | | | | 175 | |
| Leu | Tyr | Phe | Gly | Met | Trp | Lys | Thr | Thr | Phe | Ala | Trp | His | Thr | Glu | Asp |
| | | | 180 | | | | | 185 | | | | | 190 | | |
| Met | Asp | Leu | Tyr | Ser | Ile | Asn | Tyr | Leu | His | Phe | Gly | Glu | Pro | Lys | Thr |
| | | | 195 | | | | | 200 | | | | | 205 | | |
| Trp | Tyr | Val | Val | Pro | Pro | Glu | His | Gly | Gln | His | Leu | Glu | Arg | Leu | Ala |
| | 210 | | | | | 215 | | | | | 220 | | | | |
| Arg | Glu | Leu | Phe | Pro | Asp | Ile | Ser | Arg | Gly | Cys | Glu | Ala | Phe | Leu | Arg |
| 225 | | | | | 230 | | | | | 235 | | | | | 240 |
| His | Lys | Val | Ala | Leu | Ile | Ser | Pro | Thr | Val | Leu | Lys | Glu | Asn | Gly | Ile |
| | | | | 245 | | | | | 250 | | | | | 255 | |
| Pro | Phe | Asn | Cys | Met | Thr | Gln | Glu | Ala | Gly | Glu | Phe | Met | Val | Thr | Phe |
| | | | 260 | | | | | 265 | | | | | 270 | | |
| Pro | Tyr | Gly | Tyr | His | Ala | Gly | Phe | Asn | His | Gly | Phe | Asn | Cys | Ala | Glu |
| | | | 275 | | | | | 280 | | | | | 285 | | |
| Ala | Ile | Asn | Phe | Ala | Thr | Pro | Arg | Trp | Ile | Asp | Tyr | Gly | Lys | Met | Ala |
| | 290 | | | | | 295 | | | | | 300 | | | | |
| Ser | Gln | Cys | Ser | Cys | Gly | Glu | Ser | Thr | Val | Thr | Phe | Ser | Met | Asp | Pro |
| 305 | | | | | 310 | | | | | 315 | | | | | 320 |
| Phe | Val | Arg | Ile | Val | Gln | Pro | Glu | Ser | Tyr | Glu | Leu | Trp | Lys | His | Arg |
| | | | | 325 | | | | | 330 | | | | | 335 | |
| Gln | Asp | Leu | Ala | Ile | Val | Glu | His | Thr | Glu | Pro | Arg | Val | Ala | Glu | Ser |
| | | | 340 | | | | | 345 | | | | | 350 | | |
| Gln | Glu | Leu | Ser | Asn | Trp | Arg | Asp | Asp | Ile | Val | Leu | Arg | Arg | Ala | Ala |
| | | | 355 | | | | | 360 | | | | | 365 | | |

```
Leu Gly Leu Arg Leu Leu Pro Asn Leu Thr Ala Gln Cys Pro Thr Gln
    370                 375                 380
Pro Val Ser Ser Gly His Cys Tyr Asn Pro Lys Gly Cys Gly Thr Asp
385                 390                 395                 400
Ala Val Pro Gly Ser Ala Phe Gln Ser Ser Ala Tyr His Thr Gln Thr
                405                 410                 415
Gln Ser Leu Thr Leu Gly Met Ser Ala Arg Val Leu Leu Pro Ser Thr
            420                 425                 430
Gly Ser Trp Gly Ser Gly Arg Gly Arg Gly Arg Gly Gln Gly Gln Gly
        435                 440                 445
Arg Gly Cys Ser Arg Gly Arg Gly His Gly Cys Cys Thr Arg Glu Leu
    450                 455                 460
Gly Thr Glu Glu Pro Thr Val Gln Pro Ala Ser Lys Arg Arg Leu Leu
465                 470                 475                 480
Met Gly Thr Arg Ser Arg Ala Gln Gly His Arg Pro Gln Leu Pro Leu
                485                 490                 495
Ala Asn Asp Leu Met Thr Asn Leu Ser Leu
            500                 505
```

METHOD FOR IDENTIFYING COMPOUND FOR INHIBITING AN ACTIVITY OF A HISTONE LYSINE DEMETHYLASE

CROSS-REFERENCE TO RELATED APPLICATIONS

The present application is a non-provisional utility application which claims priority to U.S. Provisional Application No. 61/955,225, filed on Mar. 19, 2014, incorporated herein by reference in its entirety. The sequence listing text file, file name 2118_WWJ_SEQ, created Mar. 18, 2015, file size 38,571 bytes, is incorporated herein by reference in its entirety.

FIELD OF THE INVENTION

The present invention relates to a method for identifying a compound that inhibits an activity of a histone lysine demethylase.

DESCRIPTION OF PRIOR ART

Histone lysine demethylases (KDMs) that regulate a dynamic, reversible status of "methyl" histone codes have gained much attention. Mutations, amplifications, deletions and aberrant expression of KDMs have been identified in a variety of cancers and their roles in modulating the behaviours of cancer cells have been substantiated. As such, increasing attention has been paid to evaluate KDMs as potential therapeutic targets for cancer. There are now 8 KDM families including 28 members identified. KDM2-KDM8 constitute a large superfamily that shares a Jumonji C (JmjC) domain which functions as α-ketoglutarate (AKG) and Fe(II)-dependent demethylase. Notably, each family exhibits its exquisite substrate specificity toward different histone lysine residues, thereby effectively integrating the upstream signals and modulating the chromatin conformation.

The largest KDM4 gene family (four paralogs KDM4A-KDM4D and two pseudogenes KDM4E and KDM4F) has been shown to be an "eraser" of a repressive mark H3K9me3/me2, while its subfamily KDM4A-KDM4C also demethylates H3K36me3/me2. KDM4A and KDM4B are over expressed in a variety of cancers including prostate, breast, colorectal, lung, gastric, esophageal, lymphoma, renal cancer, and medulloblastoma. For prostate and breast cancers, this family of demethlases have the added significance in being coactivators of androgen receptor (AR) (KDM4A, B, C and D) and estrogen receptor (ER) (KDM4A and B). They function to stimulate the transcriptional potential of the receptors. KDM4B also regulates the turnover of AR. Given the important roles of AR and ER in prostate and breast carcinogenesis, KDM4A/4B are considered as promising drug targets of intervention in these malignancies.

Thus far, inhibitors for KDM4 proteins described are largely AKG analogues: N-oxalylglycines (OGAs) that inhibit KDM4A, KDM4C and KDM4D, pyridine 2,4-dicarboxylic acids (PD2s) developed based on KDM4E, and 8-hydroxyquinolines (8HQs) of which 5-carboxy-8HQ displays the highest potency on KDM4E in vitro (IC50=0.2 μM). Yet, as a prodrug, cytotoxic IC50 of PD2 is at ~mM range in cultured cells, due to its poor cell-penetrating ability, while 5-carboxy-8HQ exhibits a relatively high cytotoxic IC50 in HeLa cells (86.5 μM).

SUMMARY OF THE INVENTION

The present invention provides a method for identifying a compound which inhibits an activity of a histone lysine demethylase, comprising: (a) using a computer program to generate a three-dimensional structure of a pocket of a histone lysine demethylase, wherein the pocket comprises three sites: alpha-ketoglutarate (AKG), a methylated lysine, and a NIQ; (b) screening for a compound that interacts with the three sites of said pocket; and (c) testing the compound screened in (b) by in vitro or in vivo assay for its ability to inhibit the activity of the histone lysine demethylase, thereby identifying a compound that inhibits the activity of the histone lysine demethylase.

BRIEF DESCRIPTION OF THE DRAWINGS

FIG. 5 shows the docked conformations of (B) NSC107408 (in group 1), (C) NSC15975 (in group 2), and (D) NSC640999 (in group 3). NSC107408, NSC15975, and NSC640999 lack the interactions in the AKG site, the methylated lysine site, and the NIQ site, respectively, compared to 1,5-bis[(E)-2-(3,4-dichlorophenyl)ethenyl]-2,4-dinitrobenzene.

DETAILED DESCRIPTION OF THE INVENTION

Figure 1:
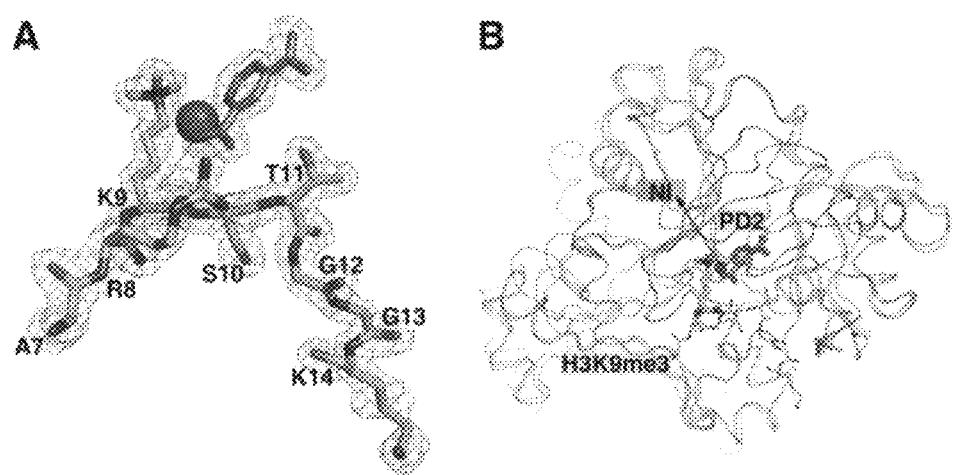
FIG. 1 shows (A) the electron density map for the Ni (II), PD2, and the H3K9me3 peptide. The 2Fo-Fc electron density maps are contoured at 1.0 σ. (B) The JmjC domain of KDM4B folds into a β-barrel structure.

As used herein in the specification, "a" or "an" may mean one or more. As used herein in the claim(s), when used in conjunction with the word "comprising", the words "a" or "an" may mean one or more than one.

The present invention identifies a selective inhibitor 1,5-bis[(E)-2-(3,4-dichlorophenyl)ethenyl]-2,4-dinitrobenzene (NSC636819) toward KDM4A/4B/4C subfamily. Kinetic and docking analyses reveal crucial binding sites of 1,5-bis[(E)-2-(3,4-dichlorophenyl)ethenyl]-2,4-dinitrobenzene unique in the KDM4A/KDM4B/KDM4C subfamily. Further, the pharmacological and genetic inhibition of KDM4A/4B significantly lowers the viability of prostate cancer cells, principally due to its potency to inhibit AR transcriptional network.

A method for identifying a compound that modulates the activity of a histone lysine demethylase having a pocket formed by residues including Gln85, Tyr133, Asp136, Tyr176, Tyr178, Phe186, His189, Glu191, Asn199, Lys207, His241, Lys242, His277 and/or Asn291, wherein the amino acid position refers to the full length histone lysine demethylase shown in SEQ ID NO: 11 or a fragment or derivative thereof; a pocket formed by Gln84, Tyr132, Asp135, Tyr175, Tyr177, Phe185, His188, Glu190, Asn198, Lys206, His240, Lys241, His276 and/or Asn290, wherein the amino acid position refers to the full length histone lysine demethylase shown in SEQ ID NO: 12 or a fragment or derivative thereof; a pocket formed by Gln86, Tyr134, Asp137, Tyr177, Tyr179, Phe187, His190, Glu192, Asn200, Lys208, His242, Lys243, His278 and/or Asn292, wherein the amino acid position refers to the full length histone lysine demethylase shown in SEQ ID NO: 13 or a fragment or derivative thereof; a pocket formed by Gln88, Tyr136, Asp139, Tyr179, Tyr181, Phe189, His192, Glu194, Asn202, Lys210, His244, Lys245, His280 and/or Asn294, wherein the amino acid position refers to the full length histone lysine demethylase shown in SEQ ID NO: 14 or a fragment or derivative thereof; or a pocket formed by Gln85, Tyr133, Asp136, Tyr176, Tyr178, Phe186, His189, Glu191, Asn199, Lys207, His241, Lys242, His277 and/or Asn291, wherein the amino acid position refers to the full length histone lysine demethylase shown in SEQ ID NO: 15 or a fragment or derivative thereof; the method comprises modeling the compound in the pocket of the histone lysine demethylase; and determining the effect of the compound on the rate or degree of methylation of a substrate of the histone lysine demethylase.

The present invention provides a method for identifying a compound which inhibits an activity of a histone lysine demethylase, comprising: (a) using a computer program to generate a three-dimensional structure of a pocket of a histone lysine demethylase, wherein the pocket comprises three sites: an alpha-ketoglutarate (AKG), a methylated lysine, and a NIQ; (b) screening for a compound that interacts with the three sites of said pocket; and (c) testing the compound screened in (b) by in vitro or in vivo assay for its ability to inhibit the activity of the histone lysine demethylase, thereby identifying a compound that inhibits the activity of the histone lysine demethylase.

As used herein, the histone lysine demethylase (KDM) comprises a KDM4A, a KDM4B, a KDM4C, a KDM4D, a KDM4E. The peptide sequence of the KDM4A is SEQ ID NO: 11. The peptide sequence of the KDM4B is SEQ ID NO: 12. The peptide sequence of the KDM4C is SEQ ID NO: 13. The peptide sequence of the KDM4D is SEQ ID NO: 14. The peptide sequence of the KDM4C is SEQ ID NO: 13. The peptide sequence of the KDM4E is SEQ ID NO: 15.

In one embodiment, the pocket of the histone lysine demethylase is formed by residues including Gln85, Tyr133, Asp136, Tyr176, Tyr178, Phe186, His189, Glu191, Asn199, Lys207, His241, Lys242, His277 and Asn291, wherein the amino acid position refers to the full length histone lysine demethylase shown in SEQ ID NO: 11 or a fragment or derivative thereof. The alpha-ketoglutarate site is defined as the cavity occupied by alpha-ketoglutarate in the active-site histone lysine demethylase shown in SEQ ID NO: 11. The alpha-ketoglutarate site is surrounded by Y133, F186, H189, E191, S197, N199, K207, W209, T271, H277, and S289 of the SEQ ID NO: 11. The methylated lysine site is defined as the cavity occupied by the methylated lysine in the active site of the histone lysine demethylase shown in SEQ ID NO: 11. The methylated lysine site is enclosed by E170, G171, V172, Y176, Y178, E191, S197, S289, T290 and N291 of the SEQ ID NO: 11. The NIQ site is defined to comprise amino acid residues N87, I72, and Q89 of the SEQ ID NO: 11.

In another embodiment, the pocket of the histone lysine demethylase is formed by residues including Gln84, Tyr132, Asp135, Tyr175, Tyr177, Phe185, His188, Glu190, Asn198, Lys206, His240, Lys241, His276 and Asn290, wherein the amino acid position refers to the full length histone lysine demethylase shown in SEQ ID NO: 12 or a fragment or derivative thereof. The alpha-ketoglutarate site is defined as the cavity occupied alpha-ketoglutarate in the active site of histone lysine demethylase shown in SEQ ID NO: 12. The alpha-ketoglutarate site is surrounded by Y132, F185, H188, E190, S196, N198, K206, W208, T270, H276, and S288 of the SEQ ID NO: 12. The methylated lysine site is defined as the cavity occupied by the methylated lysine in the active site of the histone lysine demethylase shown in SEQ ID NO: 12. The methylated lysine site is enclosed by E169, G170, V171, Y175, Y177, E190, S196, S288, T289 and N290 of the SEQ ID NO: 12. The NIQ site is defined to comprise amino acid residues N86, I71, and Q88 of the SEQ ID NO: 12.

In one embodiment, the pocket of the histone lysine demethylase is formed by residues including Gln86, Tyr134, Asp137, Tyr177, Tyr179, Phe187, His190, Glu192, Asn200, Lys208, His242, Lys243, His278 and Asn292, wherein the amino acid position refers to the full length histone lysine demethylase shown in SEQ ID NO: 13 or a fragment or derivative thereof. The alpha-ketoglutarate site is defined as the cavity occupied alpha-ketoglutarate in the active site of histone lysine demethylase shown in SEQ ID NO: 13. The alpha-ketoglutarate site is surrounded by Y134, F187, H190, E192, S198, N200, K208, W210, T272, H278, and S290 of the SEQ ID NO: 13. The methylated lysine site is defined as the cavity occupied by the methylated lysine in the active site of the histone lysine demethylase shown in SEQ ID NO: 13. The methylated lysine site is enclosed by E171, G172, V173, Y177, Y179, E192, S198, S290, T291 and N292 of the SEQ ID NO: 13. The NIQ site is defined to comprise amino acid residues N88, I73, and Q90 of the SEQ ID NO: 13.

In another embodiment, the pocket of the histone lysine demethylase is formed by residues including Gln88, Tyr136, Asp139, Tyr179, Tyr181, Phe189, His192, Glu194, Asn202, Lys210, His244, Lys245, His280 and Asn294, wherein the amino acid position refers to the full length histone lysine demethylase shown in SEQ ID NO: 14 or a fragment or derivative thereof.

In one embodiment, the pocket of the histone lysine demethylase is formed by residues including Gln85, Tyr133, Asp136, Tyr176, Tyr178, Phe186, His189, Glu191, Asn199, Lys207, His241, Lys242, His277 and Asn291, wherein the amino acid position refers to the full length histone lysine demethylase shown in SEQ ID NO: 15 or a fragment or derivative thereof.

In another embodiment, the activity is the demethylating activity.

The histone lysine demethylase (KDM) has the function for demethylating the histone code. In one embodiment, the histone code comprises a H3K9me3, a H3K9me2, a H3K36me3, and a H3K36me2. In a preferred embodiment, the KDM4A and KDM4B demethylate H3K9me3/me2.

The compounds of the present invention can also be designed by visually inspecting the three-dimensional structure of the KDM to determine more effective inhibitors. This type of modeling is generally referred to as "manual" drug design. Manual drug design can employ visual inspection and analysis using a graphics visualization program. Initially compounds are selected by manual drug design. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules.

In another embodiment, the compound that inhibits the activity of the histone lysine demethylase further is used to treat cancer.

The present invention also provides a method for treating cancer, which comprises administering an effective amount of compound and a pharmaceutically acceptable carrier to a subject in need thereof, wherein the compound has the structure of formula I:

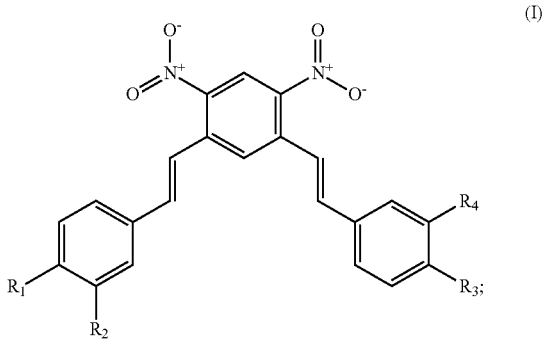

wherein $R_{1-4}$ is F, Cl, Br, I, At, hydroxyl or $C_xH_yN_zO_\alpha S_\beta$ respectively, wherein x=1-11, y=3-15, z=0-3, α=0-2 and β=0-1.

The present invention may be used to treat, alleviate, ameliorate, relieve, delay onset of, inhibit progression of, reduce severity of, and/or reduce incidence of one or more symptoms or features of a disease, disorder, and/or condition induced by the cancer. In a preferred embodiment, the method of the present invention further treats a prostate cancer.

In one embodiment, the cancer is selected from prostate cancer, breast cancer, colorectal cancer, lung cancer, gastric cancer, esophageal cancer, lymphoma, renal cancer or medulloblastoma. In a preferred embodiment, the cancer is a prostate cancer.

In another embodiment, the compound is a 1,5-bis[(E)-2-(3,4-dichlorophenyl)ethenyl]-2,4-dinitrobenzene.

A "effective amount" is an amount effective to prevent, lower, stop or reverse the development of, or to partially or totally alleviate the existing symptoms of a particular condition for which the subject being treated.

The "compound" or "1,5-bis[(E)-2-(3,4-dichlorophenyl) ethenyl]-2,4-dinitrobenzene" may be formulated for administering via sterile aqueous solution or dispersion, aqueous suspension, oil emulsion, water in oil emulsion, site-specific emulsion, long-residence emulsion, sticky-emulsion, microemulsion, nanoemulsion, liposomes, microparticles, microspheres, nanospheres, nanoparticles, minipumps, and with various natural or synthetic polymers that allow for sustained release. The compounds comprising the NRIP may also be formulated into aerosols, tablets, pills, sterile powders, suppositories, lotions, creams, ointments, pastes, gels, hydrogels, sustained-delivery devices, or other formulations used in drug delivery.

As used herein, the term "pharmaceutically acceptable carriers" are determined in part by the particular composition being administered, as well as by particular method used to administer the composition. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In one embodiment, the subject is an animal. Preferably, the subject is a mammal. More preferably, the subject is a human.

In one embodiment, the compound inhibits a cancer cell growth by inhibiting an expression of a histone lysine demethylase (KDM). In a preferred embodiment, the compound induces an apoptosis of a cancer cell by inhibiting an expression of the histone lysine demethylase (KDM). In a more preferred embodiment, the compound inhibits the demthylating function of the KDM. In another embodiment, the KDM is a KDM4A or a KDM4B.

In another embodiment, the KDM demethylates a histone. In a preferred embodiment, the histone comprises a H3K9me3, a H3K9me2, a H3K36me3, and a H3K36me2. In a preferred embodiment, the KDM4A and the KDM4B demethylate the H3K9me3 and the H3K9me2.

In one embodiment, the compound further inhibits the cancer cell growth or induces an apoptosis of a cancer cell by inhibiting an androgen receptor (AR), wherein the AR is a coactivator of the KDM4A and the KDM4B.

EXAMPLES

The examples below are non-limiting and are merely representative of various aspects and features of the present invention.

Material and Methods:

Cloning, Expression, and Purification

Human KDM4B 1-348 and KDM4A 1-347 were PCR amplified from chromosomal DNA using forward and reverse primers as follows:

| Gene | Primer sequence | SEQ ID No. |
|---|---|---|
| KDM4B 1-348 | Forward: 5'-AAA CAT ATG GGG TCT GAG GAC CAC GGC GCC-3' (NdeI) | 1 |
| | Reverse: 5'- AAA AAA CTC GGG GCT CTC GAG CTA CGT GGG CCG -3' (XhoI) | 2 |
| KDM4A 1-347 | Forward: 5'- AAA CAT ATG GCG AGC GAA AGC GAA ACT CTG -3' (NdeI) | 3 |
| | Reverse: 5'- AAA GGA TCC CTA CGT GGG CAG AGT ATG GTC-3' (BamHI) | 4 |

PCR was performed with HiFi DNA polymerase kit using a C1000 Touch™ Thermal Cycler (Bio-Rad Laboratories, Inc., USA): initial denaturation, at 95° C. for 5 min followed by 25 cycles of denaturation at 95° C. for 30 s, annealing at 55° C. for 30 s, and extension at 72° C. for 70 s. The amplified product was inserted into pET28a (Novagen, Inc., USA) to generate pET28a-KDM4B 1-348 and pET28a-KDM4A 1-347 which were introduced into *Escherichia coli*

BL21 (DE3) cells. Expression of protein was induced by addition of 0.5 mM isopropyl-β-d-thiogalacto-pyranoside (IPTG) at 16° C. for 21 h. Bacterial pellets were fractionated by sonication to collect soluble proteins in cytosolic fractions. The His6-tagged KDM4B or KDM4A proteins were purified by a nickel affinity column (Ni Sepharose™ High Performance, GE Healthcare) using the elution buffer containing 500 mM NaCl, 250 mM imidazole and 50 mM HEPES (pH 7.5). The protein was concentrated and further purified by a 16/60 Superdex 75 gel filtration column equilibrated with 50 mM HEPES pH 7.5, 500 mM NaCl. The protein purity was analyzed by SDS-PAGE analysis. Protein concentration was assayed by the Bradford method using bovine serum albumin as the standard.

Enzyme Assay

Formaldehyde dehydrogenase-coupled demethylase assay was used to determine the demethylase activity and select the potent inhibitors. All inhibitors were dissolved in dimethyl sulfoxide (DMSO) at various concentrations, and added to the mixture that the final DMSO concentration is 5%. The reagents for demethylase reactions were dissolved in HEPES buffer (50 mM, pH 7.5), with the exception of Fe(II) solutions, which were made using (NH4)2Fe(SO4)2 dissolved in 20 mM HCl to make 400 mM stock solution. All the reagents were stored at −30° C. FDH, NAD+, H-TKQTARK(Me3)STGGKAPR-OH (TR-15, H33-17K9me3, Kelowna), DMSO, and KDM4B were added first to 96-well black immune plate (SPL Life Science) and incubated together on ice for 15 min. Then the plate was put into FLUOStar OPTIMA ELISA reader (BMG LABTECH) with 37° C., and the reaction was started by adding ascorbic acid (ascorbate), Fe(II), and α-ketoglutarate (AKG) to final concentration of 50 mM HEPES, pH 7.5, 2 μM of KDM4B, 5% DMSO, 0.01 U FDH (Sigma), 1 mM NAD+, 1 mM 2-OG, 2 mM ascorbate, and 50 μM Fe(II), various concentration of H3K9me3 peptide, and the final volume was 50 μl. Each reaction was incubated at 37° C. for 30 min and the production of NADH would be detected by using the fluorescence Ex 360/Em 470.

Crystallization

Crystallization was performed by the hanging-drop vapor-diffusion method at 4° C. Equal volumes of a protein sample and the reservoir solution were mixed. Initial crystallization screening was automated using a robot Oryx8 (Douglas Instruments, UK) and the reagents of seven sets of crystallization kits: Crystal Screen I and II kits (Hampton Research), Index kit (Hampton Research), Clear Strategy Screen I and II kits (Molecular Dimension), Wizard kit (Emerald), and JB Screen classic HTS I and II kits (Jena Bioscience). Crystals of KDM4B (10 mg/ml protein, 4 mM PD2 and 5 mM H3K9me3 peptide) were grown in 0.1 M MES (pH 6.5), 0.2 M magnesium acetate, 20% (w/v) polyethylene glycol (PEG) 8000. Optimized crystals used for diffraction (12 mg/ml within 4 mM PD2 and 5 mM H3K9me3 peptide) were grown in 0.1 M MES (pH 6.5), 0.2 M magnesium acetate, 24% (w/v) polyethylene glycol (PEG) 8000. The crystal diffracted to 1.87 Å, belonged to space group P212121, and had unit cell dimensions of a=54.36, b=78.48, c=83.89 Å. The asymmetric unit contained one molecule.

X-ray Data Collection and Processing

Crystals were flash frozen in a stream of liquid nitrogen and then screened and characterized using an RU-300 rotating-anode X-ray generator (Rigaku/MSC Inc., USA) at the Macromolecular X-ray Crystallographic Laboratory of the National Tsing Hua University, Taiwan. The KDM4B.PD2.H3K9me3 dataset was collected at the SPring-8 BL12B2 beamline, Japan, with an ADSC Quantum 4R detector. All datasets were indexed, integrated, and scaled using HKL-2000. Data collection statistics are shown in Table 1.

TABLE 1

Crystallographic Data and Refinement Statistics of KDM4B · PD2 · H3K9me3

| Data Collection | |
| --- | --- |
| Beamline | SPring-8 BL-12B2[a] |
| Wavelength (Å) | 1.0000 |
| Space group | $P2_12_12_1$ |
| Cell dimensions | |
| a, b, c (Å) | 54.4, 78.5,83.9 |
| α, β, γ (°) | 90.0, 90.0,90.0 |
| Resolution limit (Å) | 30-1.87 |
| Unique reflections | 30463 |
| Completeness (%)[b] | 99.4 (98.0) |
| Avg I/σ(I)[b] | 31.2 (6.0) |
| $R_{merge}$ (%)[b,c] | 4.3 (36.8) |
| Redundancy[b] | 12.5 (11.2) |
| Refinement | |
| Resolution limit (Å) | 28.67-1.87 |
| Number of atoms | 3125 |
| Protein atoms | 2768 |
| Solvent atoms | 285 |
| Ligand atoms | 72 |
| Estimated coordinate error (Å) | 0.142 |
| $R_{work}/R_{free}$[d,e] | 17.6/22.5 |
| Overall B-factor (Å²) | 28.01 |
| RMSD bond lengths (Å)[f] | 0.012 |
| RMSD bond angles (°)[f] | 1.39 |
| Ramachandran Analysis (%)[g] | |
| Favored | 95.9 |
| Allowed | 3.8 |
| Disallowed | 0.3 |

[a]BL-12B2 Taiwan beamline at SPring-8, Hyogo, Japan
[b]Values in parentheses refer to statistics in the highest-resolution shell.
[c]$R_{merge} = \Sigma|I_{obs} - <I>|/\Sigma I_{obs}$.
[d]$R_{work} = \Sigma|F_{obs} - F_{calc}|/\Sigma F_{obs}$, where $F_{obs}$ and $F_{calc}$ are the observed and calculated structure-amplitudes, respectively.
[e]$R_{free}$ was computed using 5% of the data assigned randomly.
[f]Root mean square deviation.
[g]Estimated standard uncertainties based on maximum likelihood.

Structure Determination and Refinement

Crystallographic refinement used the maximum-likelihood target function module in REFMAC5. The KDM4B.PD2.H3K9me3 structures were constructed by MOLREP with the KDM4A (PDB: 2YBS) as the template and were refined using REFMAC5 coupled with ARP/wARP, which automatically added water molecules. The 2Fo-Fc electron density maps were generated by FFT and plotted by PyMOL. The validities of the KDM4B.PD2.H3K9me3 structure were assessed by PROCHECK.

Structural Comparison

The KDM4B structure was compared with protein structures in the DALI server. The structures of KDM4A.H3$_{1-17}$K9me3 (PDB code: 2P5B), KDM4B.PD2 (PDB code: 4LXL; this study), KDM4C.OGA (PDB code: 2XML), KDM4D.AKG.H3$_{6-15}$K9me3 (PDB code: 4HON), and KDM4E (PD2; PDB code: 2W2I) were superimposed by LSQMAN in O. ESPript was used for the combined sequence and secondary structure alignments and Figure preparation. PyMol was used to prepare the figures.

Virtual Screening and Molecular Modeling

The binding site for virtual docking screening of putative inhibitors was prepared by including protein atoms located ≤10-Å-radius sphere centered around the bound ligand of KDM4A (PDB code 2YBK. The present invention utilized GEMDOCK to screen the NCI database (236,962 compounds). Top ranked, available compounds were selected for testing in the KDM4A/KDM4B inhibitory assay.

Molecular Modeling

Figure 12:
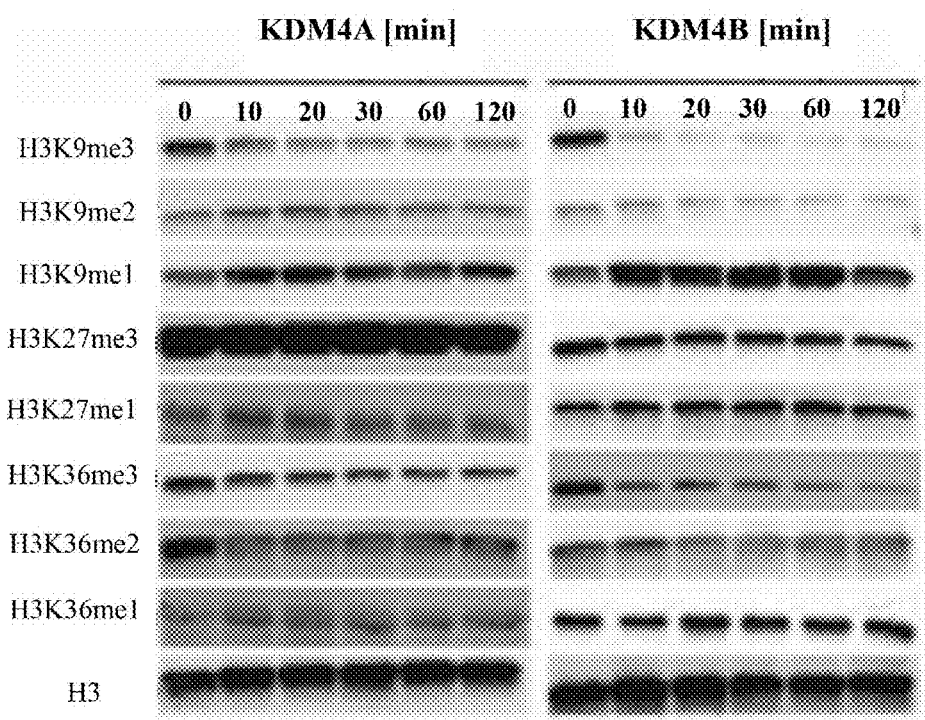
FIG. 12 shows top five results of the self-docking tests for the KDM4B.PD2 complex model. Self-docking test of KDM4B (PDB code: 4LXL) is a complex structure within PD2 and H3K9me3. The top five docking poses are shown as stick. The reference pose is shown as ball-and-stick. Ni is shown as a sphere.

Discovery Studio v3.0 (Accelrys Inc., USA) was used to prepare, energy minimize, and refine a KDM4B model for molecular dynamics. The default parameters of ChiRotor were used to optimize side-chain conformations. Energies of the protein models were further minimized using CHARMm. 1,5-bis[(E)-2-(3,4-dichlorophenyl)ethenyl]-2,4-dinitrobenzene was then docked into KDM4B by GEMDOCK, a robust flexible ligand docking tool, was first used in conjunction with its default settings to generate conformations and carry out a docking analysis for ligand-containing KDM4B. Top 10 of compounds ranked by the docking energy were derived. CDOCKER with CHARMm forcefield was used to refine the docked models. To estimate the practicability of the proposed docking procedure, the present invention performed self-docking against the co-crystal KDM4B-PD2 structure (PDB code: 4LXL). Top five docked poses with minimum RMSD≤1 Å were derived (FIG. 12). The average of RMSD for self-docked poses of KDM4B-PD2 is 0.86 Å.

Cell Culture

Primary PrEC cells were purchased from Clonetics (Walkersville, Md.) and cultured in serum-free prostate epithelial cell growth medium following the vendor's directions. Cell lines RWPE1, LNCaP (LNCaP-FGC), CWR22Rv1 (22Rv1), VCaP, DU145, PC3 (all purchased from ATCC), and PNT2 (Sigma Aldrich, Mo.), were cultured under condition as recommended. CWR-R1 cell (40) and LNCaP derived C4-2, C4-2B cells were cultured in RPMI1640 medium containing 10% FBS.

RNA Interference and Quantitative RT-PCR

Lentiviral vector pLKO.1 carrying sequences encoding a shRNA that specifically targets KDM4A and KDM4B gene (TRC library Clone ID TRCN0000234910 and TRCN000018014) were co-transfected with viral packaging plasmids in 293T cells to generate the shRNA lentiviral particles. Empty pLKO.1 plasmid was used as negative control. The lentiviral supernatant was collected after 48-hr transfection and concentrated by Lenti-X Concentrator (Clontech, Calif.). The precipitated viral particle was resuspended in fresh RPMI1640 medium with 10% FBS for subsequent LNCaP infection and transduced into LNCaP cells for 72 hrs. Cells were then harvested and total RNA was isolated, followed by cDNA synthesis and real-time PCR analysis using iQ5 iCycler thermal cycler (Bio-Rad, Calif.). Threshold cycle values were normalized against actin transcript level. Individual samples were performed in triplicate and converted to relative gene expression using QGene96 software. Primer sequences used are as follows:

| Gene | Primer sequence | SEQ ID No. |
|---|---|---|
| KDM4A | Forward: 5'- AGG AGA GTG AAC TGC CTC CA -3' | 5 |
| | Reverse: 5'- GGT CTC CTT CCT CTC CAT CC -3' | 6 |
| KDM4B | Forward: 5'- TCA CGC AGT ACA ATA TCC AG -3' | 7 |
| | Reverse: 5'- TCG TCA TCA TAC AAA GAG CC -3' | 8 |
| actin | Forward: 5'- GTA CCA CTG GCA TCG TGA TGG ACT -3' | 9 |
| | Reverse: 5'- CCG CTC ATT GCC AAT GGT GAT -3' | 10 |

Cell Proliferation Assay

LNCaP cell was seeded in 48-well plate one day prior to lentivirus infection. After subjected to the shRNA lentivirus (day 0), cell proliferation was measured every two days by MTT colorimetric assay according to the manufacturer's instruction (Roche, Ind.).

Immunoblotting and Flow Cytometry

Total cell lysates were obtained by lysing the cell with buffer (50 mM Tris-HCl pH7.5, 150 mM NaCl, 0.5% Triton X-100, 10% glycerol, 1 mM EDTA, protease inhibitors) for 15 min on ice, followed by 10 min of sonication cycle (30 sec on, 30 sec off) on ice. The level of total histone H3 and trimethylated histone H3 Lys9 was analyzed by western blotting using anti-histone H3 and anti-H3K9me3 antibodies (Abcam, Mass.). Cells treated with mock and the inhibitor were harvested and fixed by 70% ethanol for >4 hours at −20° C., followed by propidium iodide (Sigma Aldrich) staining. The DNA content was analyzed by Becton Dickinson FACScan flow cytometry, and the sub-G1 population was quantified by WinMDI 2.9.

Microarray

LNCaP cells treated with mock and the 1,5-bis[(E)-2-(3,4-dichlorophenyl)ethenyl]-2,4-dinitrobenzene inhibitor for 3 days were harvested and the total RNA was extracted using Trizol reagent (Life Technologies, N.Y.). Microarray analysis was performed by the University of California Davis Cancer Center Gene Expression Resource, using Affymetrix Human Genome U133A (HG-U133A) GeneChip arrays (Affymetrix, Calif.), which permit expression analysis of the entire Genbank RefSeq database. Array scanning and generation of raw signal data files were done with GeneChip Operating Software (Affymetrix). Subsequent data analysis was done by GeneSpring (Agilent Technologies, Calif.) and DAVID Bioinformatic Resources 6.7 (NIH).

Results:

KDM4B.PD2.H3K9me3 Crystal Structure

In an effort to understand the detailed structure-function relationship of KDM4B at an atomic resolution, the recombinant JmjC domain of KDM4B was subjected to crystallization in the presence of a peptide, Ni(II), and AKG or PD2. After extensive trials, a well-diffracting crystal was found to consist of a large piece of residual density in the binding pocket, which could be modeled as the H3K9me3 peptide, an inhibitor PD2 and Ni (FIG. 1A). The final crystal structure shows a 1.87 Å-resolution monomer (R=21.8%, $R_{free}$=26.2%) that consisted of the KDM4B catalytic domain (residues 9-337), PD2, and an H3K9me3 peptide (residues 7-14) within the active site (Table 1). A Ni(II) ion was observed to be located on a site corresponding to the Fe(II) position on the bottom of the catalytic pocket. The JmjC domain of KDM4B folded into a β-barrel structure, characteristic of members in the KDM4 family (FIG. 1B). Superposition of KDM4A.OGA.H3K9me3 (PDB code:

2Q6), KDM4B.PD2.H3K9me3, KDM4C.OGA (PDB code: 2XML), and KDM4D.AKG.H3K9me3 (PDB code: 4HON) showed limited conformational change in overall Cα atoms of the JmjC domain. RMSD between KDM4A and KDM4B was 0.54 Å (residues 9-337 of KMD4B).

Figure 10:
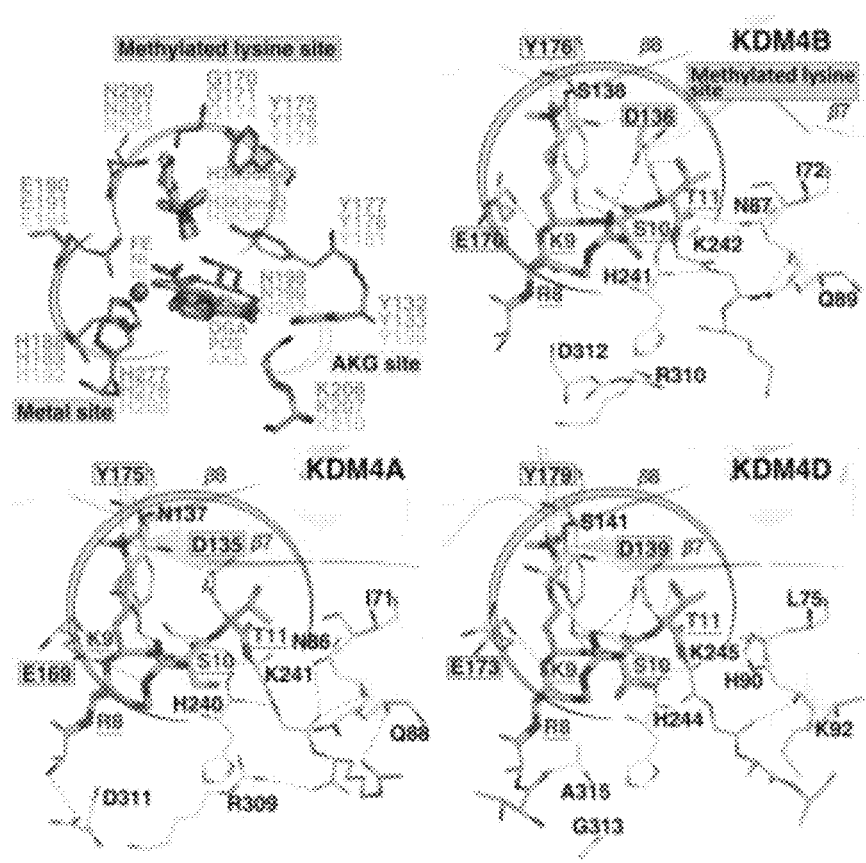
FIG. 10 shows the binding pocket in KDM4s. Strictly conserved residues that bind to Fe(II) (H189, E191 and H276 in KDM4B) and AKG(Y133, N199, K207) are shown (upper left). Superposition of H3K9me3 liganded structures reveals four strictly conserved residues of KDM4s (D136, E170, Y176, and K242 in KDM4B) make contacts with the peptide at R8 (−1), K9, S10 (+1) and T11 (+2) positions. PDB used in the left-top figure are: KDM4A (PDB: 2OQ6); KDM4B (PDB: 4LXL); and KDM4D (PDB: 4HON). H bonds (<3.5 Å) are shown as dash lines.

In the active site, PD2 was situated at a position nearly overlapped with AKG in which one of its carboxyl moieties contacted with H189, E191 and K242, while the other made H bonds with Y133 and K207, similar to those that contacted with AKG (Y132, N198, and K206 in KDM4A). Ni(II) that occupied the site of Fe(II) made contacts with three strictly conserved residues (H189, E191, and H277 in KDM4B). G171, Y176, T290, and N291 in KDM4B that surround the methylated lysine were also strictly conserved (FIG. 10).

Figure 2:
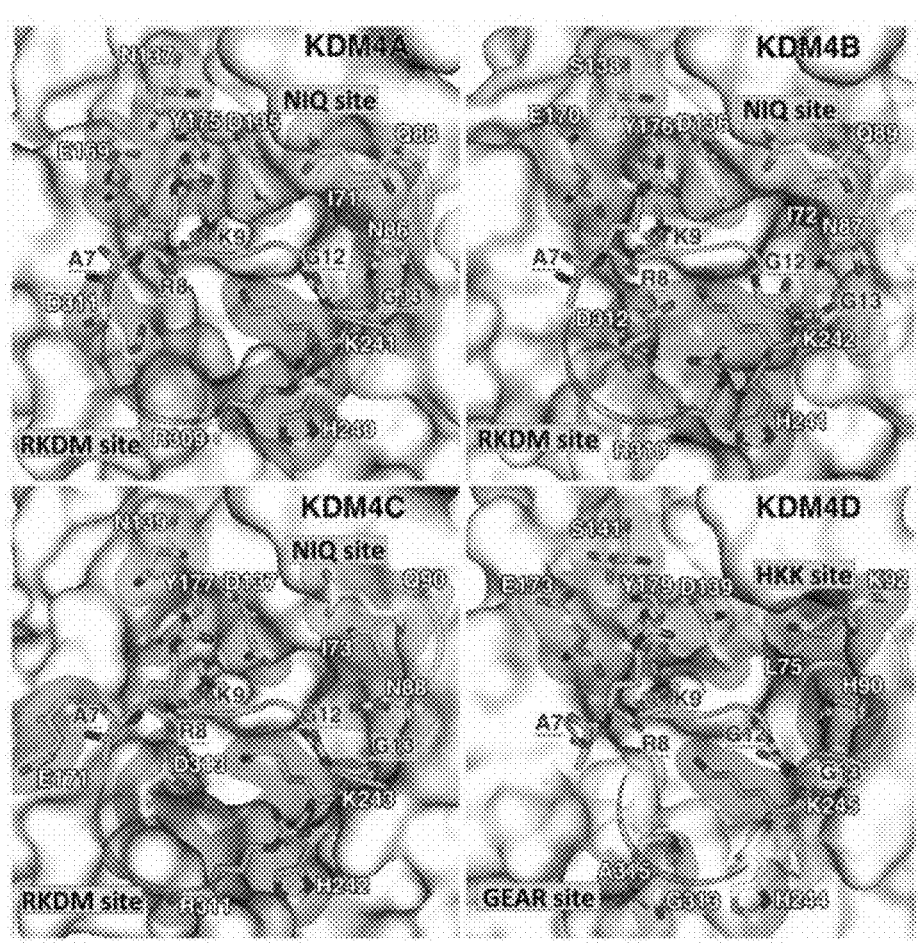
FIG. 2 shows the differential ligand binding region between KDM4A/KDM4B/KDM4C and KDM4D. Superposition of KDM4A, KDM4B, KDM4C, and KDM4D reveals two heterogeneous regions, RKDM and NIQ. Surface representation of KDM4A, KDM4B, and KDM4D shows that the RKDM, NIQ regions and a crucial isoleucine (KDM4A, I71; KDM4B, 172) make several contacts with the peptide at (−2) and (+3, +4) sites in KDM4A and KDM4B, respectively. The corresponding GEAR and HKK sites deviate away from H3K9me3. PDB used in this Figure are: KDM4A (PDB: 2OQ6); KDM4B (PDB: 4LXL); KDM4D (PDB: 4HON).

The most prominent feature of the KDM4 family was its potent catalytic activity toward H3K9me3/me2. Analysis of superimposed H3K9me3 liganded structures including KDM4A, KDM4B, and KDM4D [KDM4A. Fe(II).OGA.H3K9me3 (PDB code: 2OQ6), KDM4B.Ni(II).PD2.H3K9me3 (this study; PDB code: 4LXL), KDM4D.Ni(II).2-OG.H3K9me3 (PDB code: 4HON)] revealed a conserved region to accommodate R8 (−1) and the methylated K9 of H3. Notably, three conserved residues (KDM4A: D135, E169, Y175; KDM4B: D136, E170, Y176; KDM4D: D139, E173, Y179) from β7 and β8 made H contacts with the guanidinium group of R8, the peptide O and N atoms of K9 and the peptide N atom of T11 from H3. In the interior of this cleft, a lysyl side chain (KDM4A: K241; KDM4B: K242; KDM4D: K245) forms a strong bond to the peptide O atom of S10 (FIG. 10), hence together properly orienting the H3K9me3/me2 for similarly efficient catalysis in KDMs. Interestingly, the KDM4A/KDM4B/KDM4C subfamily but not KDM4D exhibited additional specificity to demethylate H3K36me3/me2. Consistent with the structural analysis for KDM4D, the present invention observed two heterogeneous regions in KDM4B accounting for the substrate specificity: (1) RKDM vs. GEAR and (2) NIQ vs. HKK (FIG. 2).

The RKDM site (residues 310-313 in KDM4B) from a long U-shaped loop resided near the (−1, −2) site of the peptide-binding cleft. The aspartate side chain of RKDM (D311 in KDM4A) faced toward the peptide (−1, and −2 sites) and could make contacts with the peptide (FIG. 2). Additionally, the long and positively charged side chain of R from RKDM contributed to contact with the plus side of the peptide as demonstrated in two liganded structures: KDM4A.AKG.H3K9 (PDB code: 2Q8C) [KDM4A/R309 (NH1)-H3/G12 (O): 3.8 Å] and KDM4A.N-oxalylglycine.H3K36 (PDB code: 2P5B) [KDM4A/R309 (NH1)-H3/H39 (N): 3.8 Å]. A subtle difference was also noted at the other side of this U loop between KDM4A and KDM4B; there was a T308-D236 contact in KDM4B but not in KDM4A (the corresponding residues are S307 and E235). In contrast, the GEAR motif deviated away from the peptide-binding cleft, hence no contacts with the peptide.

The other region was NIQ site from the β4-β5 segment shared in KDM4A/KDM4B/KDM4C (residues 87-89 in KDM4B) while KDM4D had HKK at the corresponding region. Q89 was noted to contact with H3H39 and R40 (+3 and +4), whereas KDM4D consisted of HKK with positively charged side chains at the corresponding site (FIG. 2), which was likely to yield steric hindrance and electrostatic repulsion against H39 and R40 of H3K36me3. I71 that was nearby NIQ (KDMA, I71; KDM4B, 172) also played a crucial role (Krishnan and Trievel, 2013).

The present invention used the formaldehyde dehydrogenase (FDH)-coupled continuous fluorescent demethylase method to assess the enzymatic activity of the recombinant KDM4A and KDM4B expressed in *Escherichia coli*. Using an H3K9me3 peptide (residues 3-17) as the substrate, KDM4A and KDM4B exhibited comparable catalytic activity (Table 2), consistent with Hillringhaus et al. The present invention were able to measure the kinetic parameters with an H3K36me3 peptide (H331-41K36me3) and obtained an analogous $k_{cat}$ value while a higher $K_m$ value as compared with those with the H3K9me3 peptide, suggesting that KDM4A/4B had a lower binding affinity toward H3K36me3 than H3K9me3.

TABLE 2

Kinetic parameters for KDM4A and KDM4B using $H3_{3\text{-}17}K9me3$ or $H3_{31\text{-}41}K36me3$ as the substrate.

| KDM4 | $k_{cat}$ (s$^{-1}$) | $K_m$ (μM) | $k_{cat}/K_m$ (s$^{-1}$μM$^{-1}$) |
|---|---|---|---|
| $H3_{3\text{-}17}K9me3$ | | | |
| KDM4A | 0.017 ± 0.001 | 92.5 ± 5.9 | 1.8 × 10$^{-4}$ |
| KDM4B | 0.014 ± 0.001 | 88.3 ± 8.6 | 1.6 × 10$^{-4}$ |
| $H3_{31\text{-}41}K36me3$ | | | |
| KDM4A | 0.015 ± 0.001 | 169.9 ± 19.9 | 8.8 × 10$^{-5}$ |
| KDM4B | 0.013 ± 0.001 | 138.5 ± 14.1 | 9.4 × 10$^{-5}$ |

Figure 11:
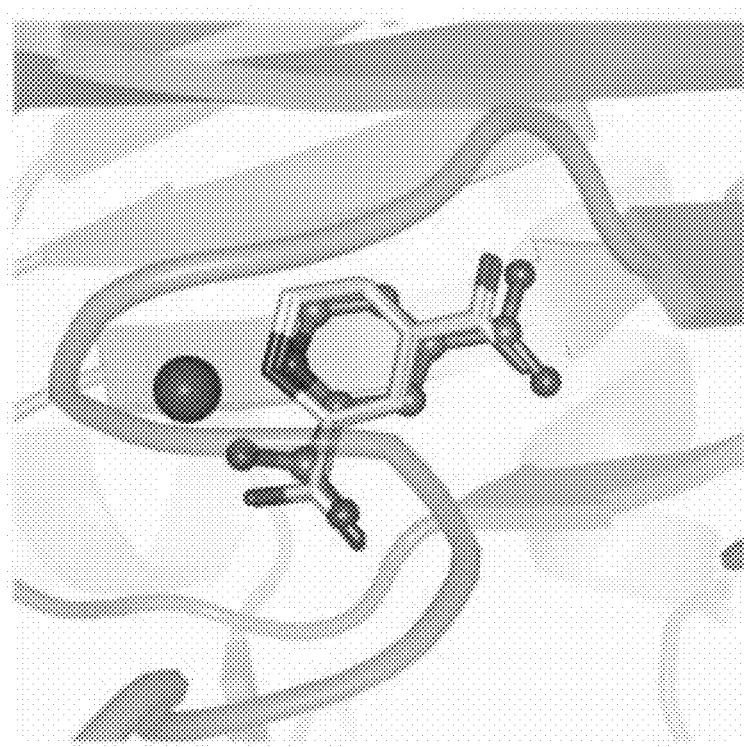
FIG. 11 shows the analysis of KDM4A and KDM4B that demethylate H3K9me3/me2 and H3K36/me3/me2 of histones but not H3K27me3/me1. Demethylation of calf thymus histones by KDM4A and KDM4B is detected by various antisera as indicated. Histones are incubated without or with KDM4A/KDM4B for a certain time as indicated.

The present invention further utilized calf thymus histones as the substrate and probed for H3K9, H3K27 and H3K36me3/me2/me1 in the presence of the recombinant KDM4A or KDM4B using western blotting analysis. As shown in FIG. 11, the signal of H3K9me3/me2 was significantly reduced while that of H3K9me1 increased in the presence KDM4A (upper panel) or KDM4B (lower panel) via a time-dependent manner as compared with the controls, indicating an active KDM4A/KDM4B form to remove the methyl group from H3K9me3/me2. For H3K36 signal, a longer time was needed to remove the signal of H3K36me3/me2. No difference was found for H3K27me3 or H3K27me1. These results collectively suggested that KDM4A and KDM4B demethylated H3K9me3/me2 more efficiently than did H3K36me3/me2 and that there was no activity toward H3K27me3/me2/me1, confirming the results in Table 2.

Figure 3A:
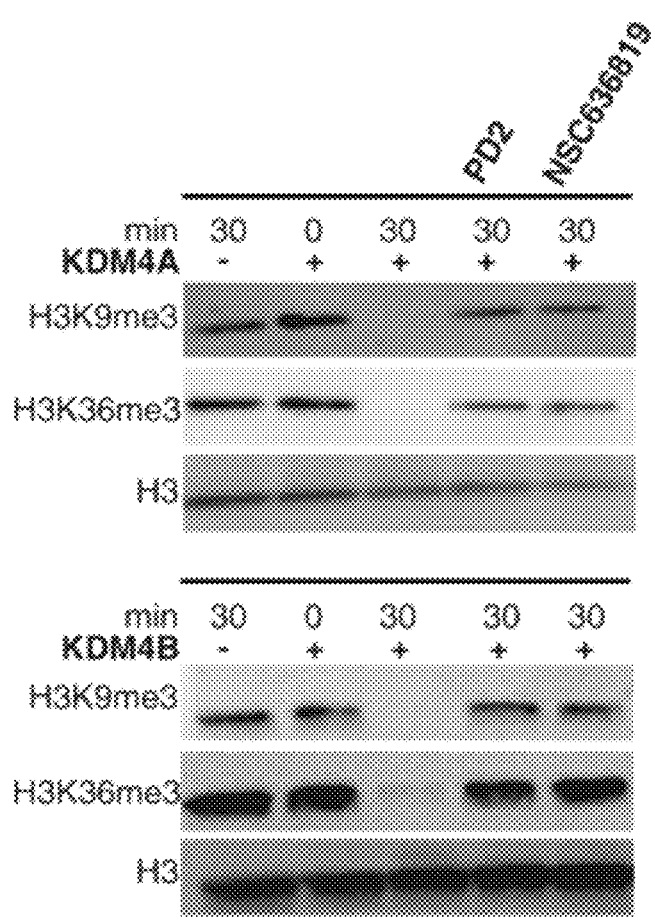
FIG. 3(A) shows demethylation of calf thymus H3 by bacteria-expressed KDM4A (upper panel) and KDM4B (lower panel) determined in the presence of 1,5-bis[(E)-2-(3,4-dichlorophenyl)ethenyl]-2,4-dinitrobenzene by western blotting analysis. H3 lysine modifications are probed with H3K9me3 and H3K36me3 antisera, respectively.
Figure 3B:
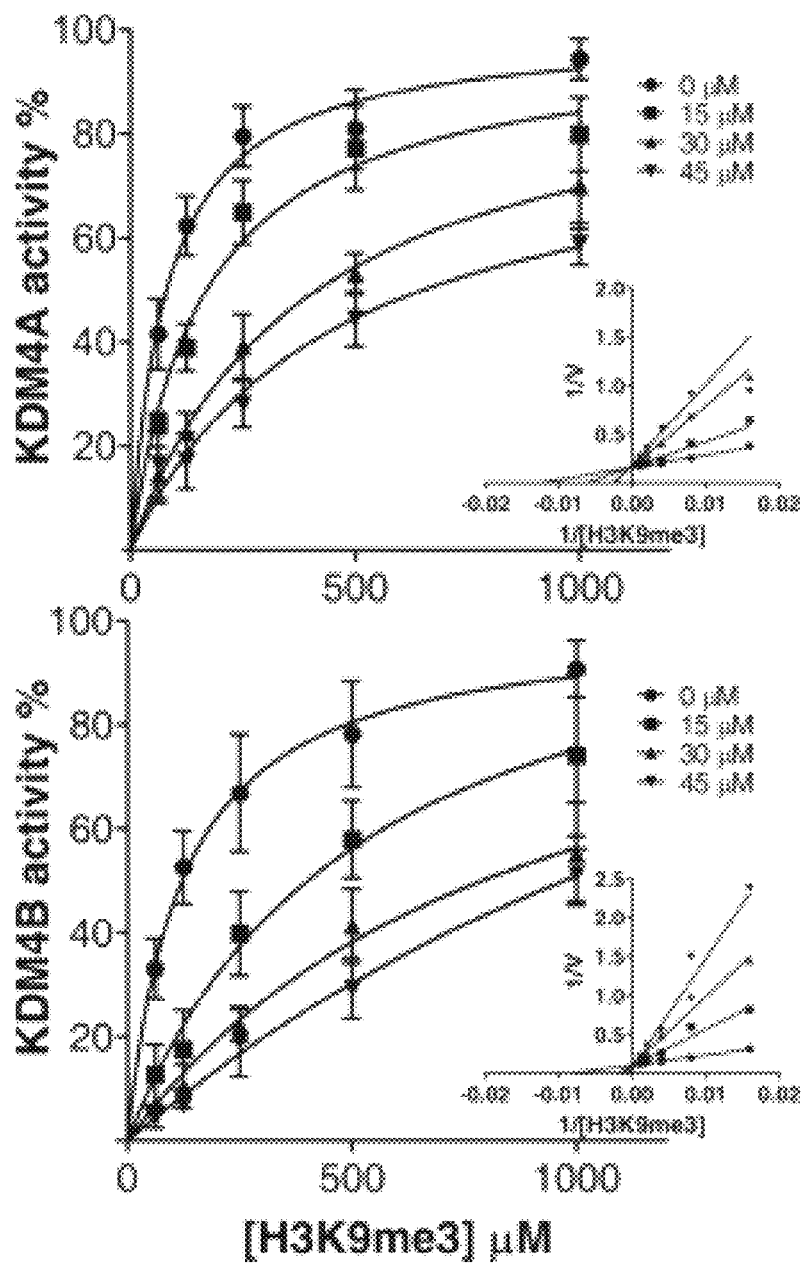
FIG. 3(B) shows inhibition kinetics of KDM4A/4B demethylation activity by 1,5-bis[(E)-2-(3,4-dichlorophenyl)ethenyl]-2,4-dinitrobenzene. The inset in each panel shows the double reciprocal form, where the 1/relative activity is plotted versus 1/[H3K9me3] at various fixed concentrations of the inhibitor.

Virtual Screening to Identify 1,5-bis[(E)-2-(3,4-dichlorophenyl)ethenyl]-2,4-dinitrobenzene as a Novel Active-Site Inhibitor Toward KDM4A and KDM4B The present invention utilized GEMDOCK to screen for putative hits against the NCI database. The known inhibitor PD2 was used as a positive control which showed significant inhibition [21% (KDM4A) and 24% (KDM4B) of residual activity]. Of the selected 10 top-ranked compounds, 1,5-bis[(E)-2-(3,4-dichlorophenyl)ethenyl]-2,4-dinitrobenzene exhibited the highest inhibitory effect toward both KDM4A (28%) and KDM4B (35%) (Table 3). To confirm the FDH-demethylase coupled results, the present invention utilized histones as the substrate and probed for H3K9me3 and H3K36me3 in the absence or presence of the recombinant KDM4A or KDM4B using western blotting analysis. FIG. 3A shows that PD2 and 1,5-bis[(E)-2-(3,4-dichlorophenyl)ethenyl]-2,4-dinitrobenzene indeed blocked the demethylation activity. Further kinetic inhibition characterization of 1,5-bis[(E)-2-(3,4-dichlorophenyl)enthenyl]-2,4-dinitrobenzene demonstrated a competitive inhibitory mode against $H3_{3\text{-}17}K9me3$ for KDM4A [IC50=6.4 μM; Ki (H3K9me3)=5.5 μM; FIG. 3B). KDM4B also showed analogous inhibition kinetics [IC50=9.3 μM; Ki (H3K9me3)=3 μM). These results together provide strong evidence that 1,5-bis

[(E)-2-(3,4-dichlorophenyl)ethenyl]-2,4-dinitrobenzene was a potent selective active-site inhibitor.

The De Novo Link protocol of Discovery Studio v3.0 (Accelrys Inc., USA) was used to suggest modifications and additions to the specific CL functional group of the docked NSC636819 in order to enhance binding to the KDM4B. This approach suggested modifications to a ligand scaffold to increase binding by placing fragments from the specified Ludi library into the specified binding site in accordance of the Ludi-generated interaction map.

The parameters used were as follows. Four CL atoms of the NSC636819 were defined as linked atoms with KDM4B as an input receptor and set an input sphere which includes whole Jmjc. Ludi-based fragment libraries were used here as input fragment libraries.

Figure 14:
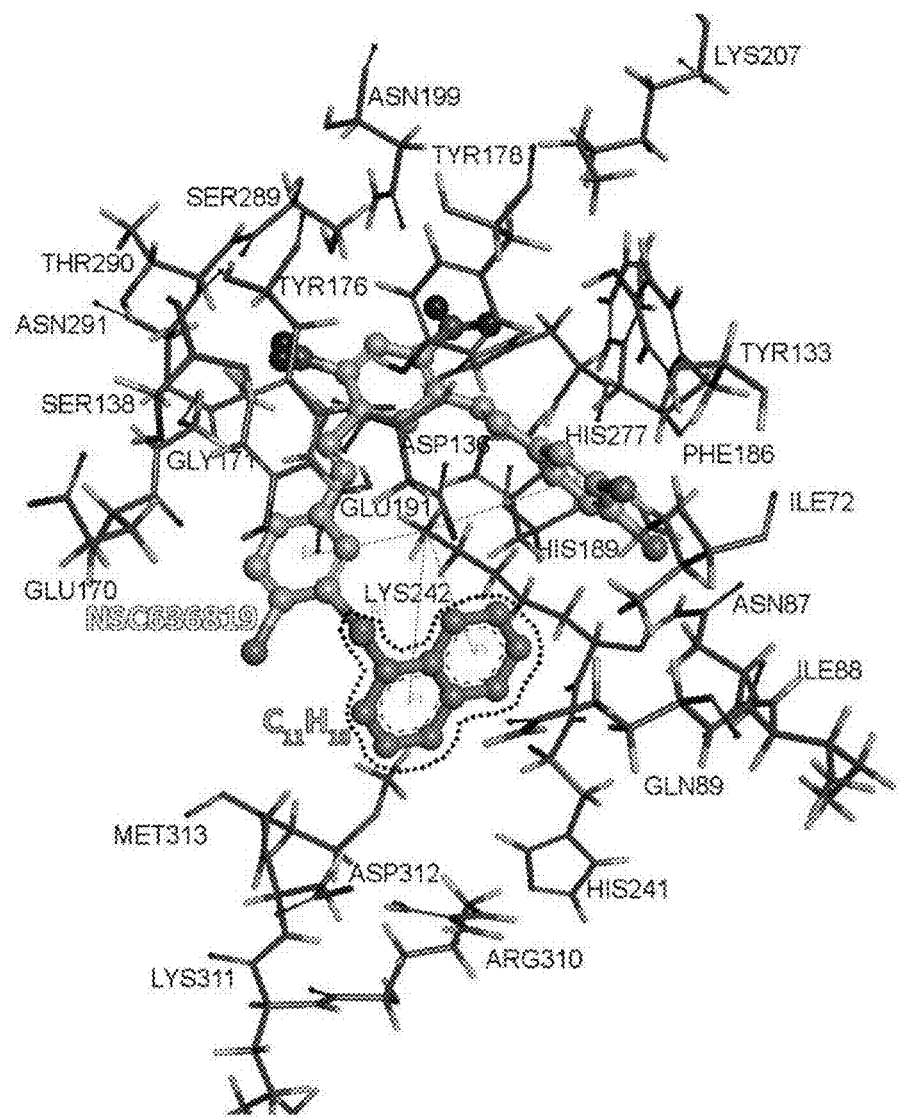
FIG. 14 is an illustration of linked T01 functional group. When the original CL atom of the R2 group is replaced by the T01 fragment, the Naphthalene-like group generates two cation-pi interaction against the LYS242 residues of KDM4B to stabilize interactions of the receptor-ligand complex.

Then the simulated results showed that 54, 94, 11 and 3 for R1, R2, R3 and R4 groups respectively. The T01 ($C_{11}H_{10}$) fragment was illustrated as an example to show the enhanced binding capability due to additional cation-Pi interactions (See FIG. 14).

Figure 4A:
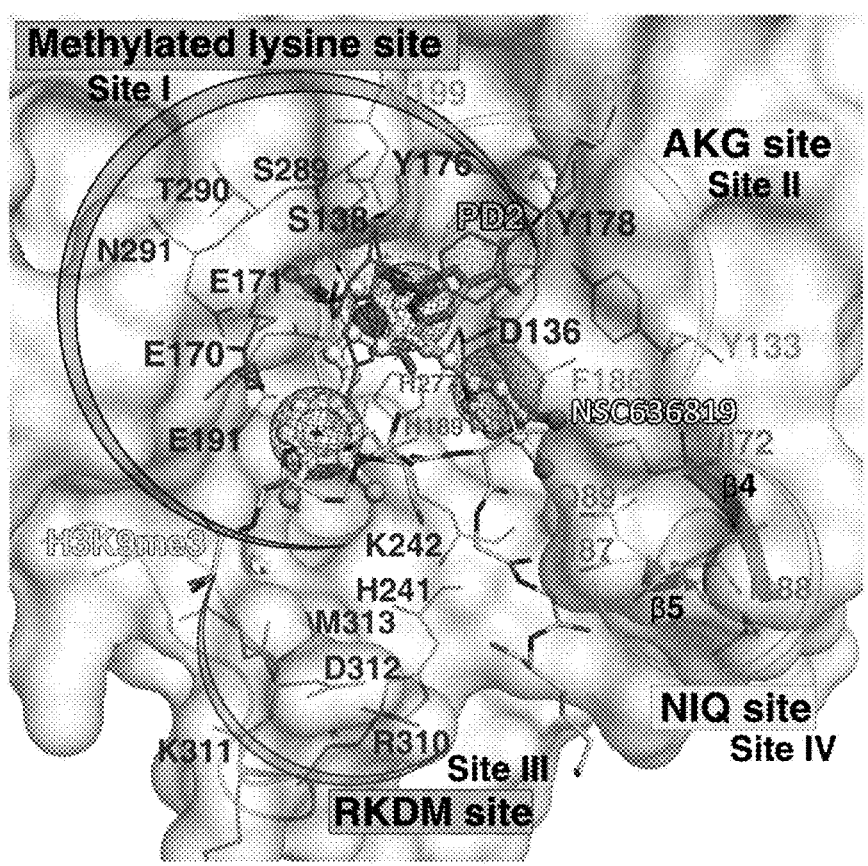
FIG. 4(A) shows surface representation of superimposed KDM4B.PD2.H3K9me3 and KDM4B.1,5-bis[(E)-2-(3,4-dichlorophenyl)ethenyl]-2,4-dinitrobenzene complexes. PD2 and H3K9me3 are drawn as stick models. 1,5-bis[(E)-2-(3,4-dichlorophenyl)ethenyl]-2,4-dinitrobenzene is show as ball-and-stick models. AKG site is labeled as site II, methylated lysine site as site I, RKDM as site III and NIQ as site IV.
Figure 4B:
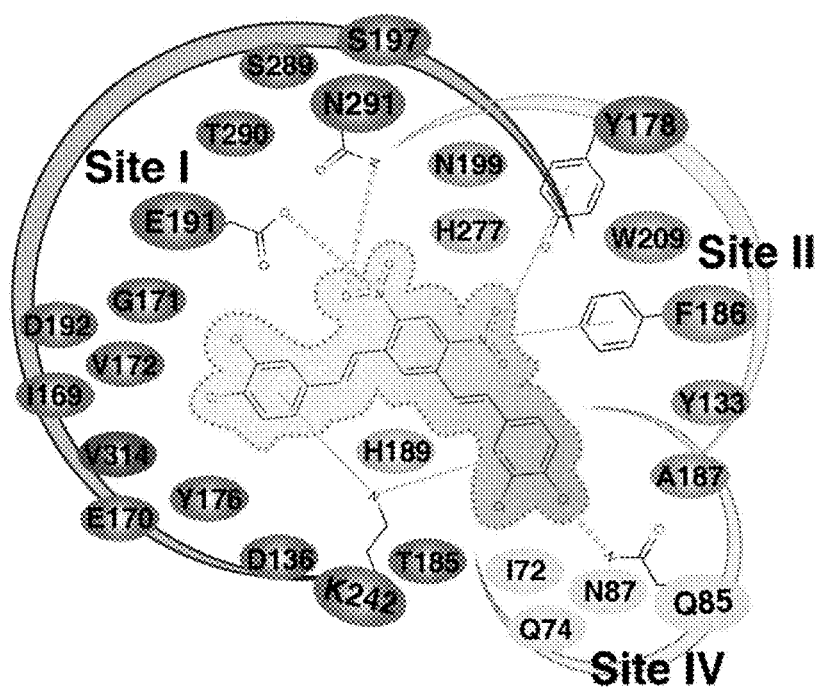
FIG. 4(B) shows schematic representation of interactions between 1,5-bis[(E)-2-(3,4-dichlorophenyl)ethenyl]-2,4-dinitrobenzene and KDM4B.
Figure 4C:
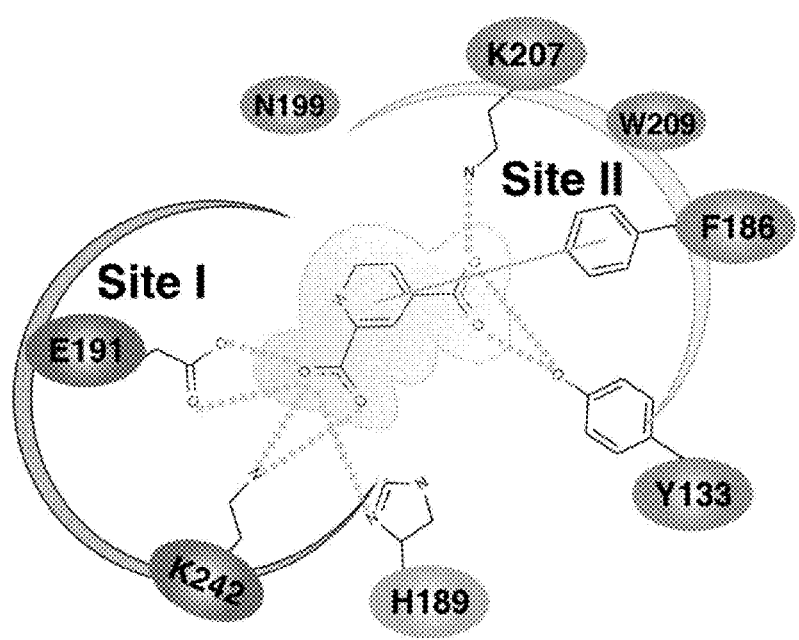
FIG. 4(C) shows schematic representation of interactions between PD2 and KDM4B. The hydrogen-bonding contacts are shown as broken lines.

The KDM4B.1,5-bis[(E)-2-(3,4-dichlorophenyl)ethenyl]-2,4-dinitrobenzene Complex Model An in silico approach was used to generate KDM4B.1,5-bis[(E)-2-(3,4-dichlorophenyl)ethenyl]-2,4-dinitrobenzene complex model by means of energy minimization and molecular dynamics simulations (FIG. 4). Given the model, 1,5-bis[(E)-2-(3,4-dichlorophenyl)ethenyl]-2,4-dinitrobenzene was situated at a position that occupied across three sites: the AKG site (e.g., H189, E191, and H277), the key lysine binding region (e.g., D136, E170, Y176, K242), and a portion of the H3K36-specific NIQ region (e.g., 172, Q85, N87) (FIG. 4). Of note, the middle benzene ring with two nitro groups reached the terminal methylated N(ε) position as well as Fe(II) position. The other two 1,2-dichlorobenzene rings were situated at the (0) and (+2) sites of the peptide-binding cleft, thereby specifically inhibiting KDM4A and KDM4B activity. Thus, 1,5-bis[(E)-2-(3,4-dichlorophenyl)ethenyl]-2,4-dinitrobenzene represented a novel KDM4A and KDM4B-specific inhibitor.

Figure 5:
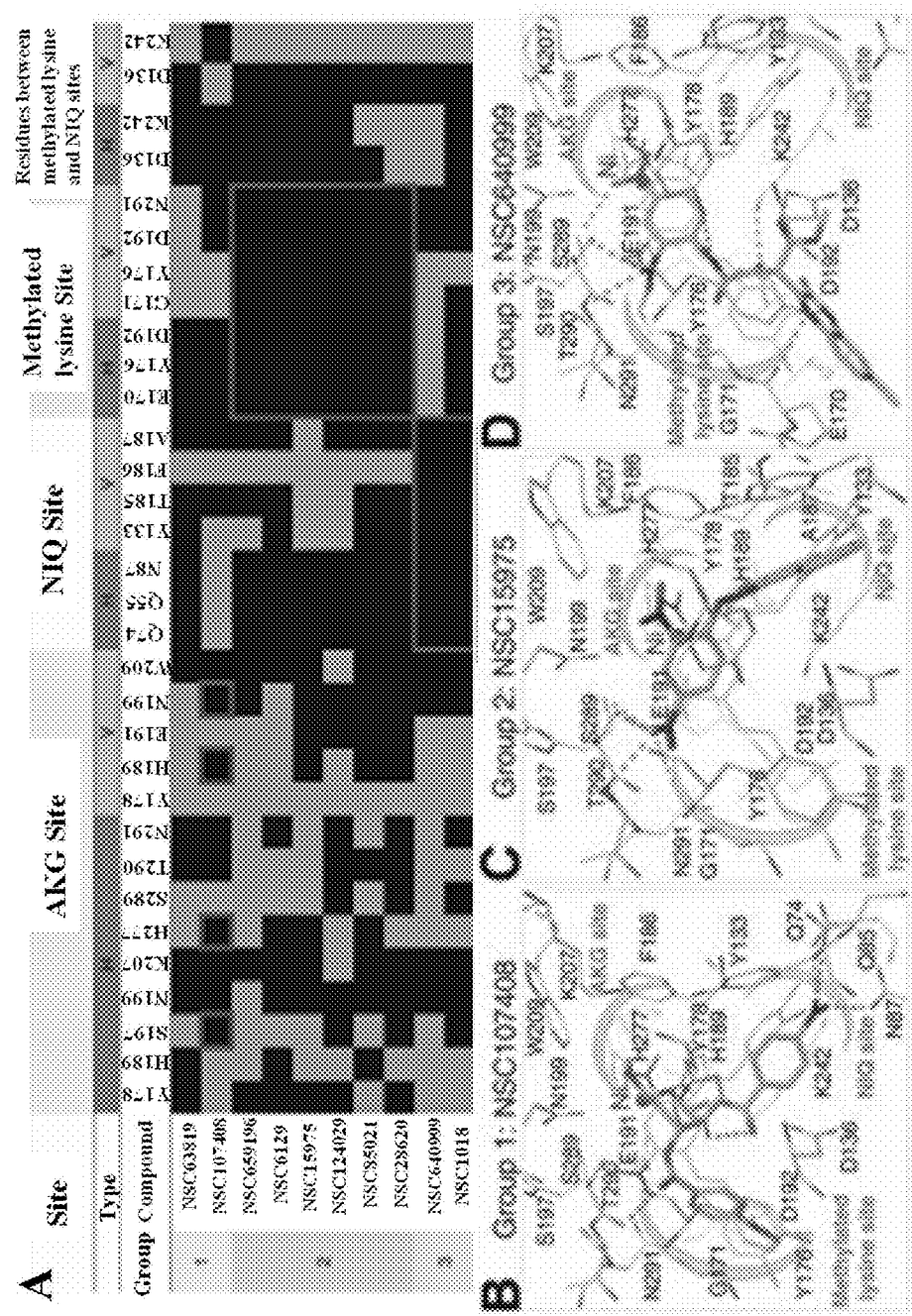
FIG. 5 shows (A) interaction profiles between residues from KDM4B and compounds. These compounds are divided into three groups based on their docked locations. The profile contains two interaction types [hydrogen-bonding (H) and van der Waals (V)]. A cell is colored in gray if a compound yields hydrogen-bonding or van der Waals interaction with a residue; otherwise, the cell is colored in black.

The present invention next compared the interactions of all tested compounds based on their docking poses. Three groups were classified: group 1 included all three sites (AKG, the methylated lysine, and NIQ); group 2 included AKG and the NIQ sites; and group 3 consisted of AKG and the methylated lysine sites (FIG. 5). Overall, compounds in group 2 and group 3 had low to modest inhibitory effects compared with 1,5-bis[(E)-2-(3,4-dichlorophenyl)ethenyl]-2,4-dinitrobenzene from group 1, suggesting the positive contribution of contacts from all three sites (FIG. 5). Above all, the meta-positioned $NO_2$ moieties on the benzene ring that occupied at the AKG and the methylated lysine sites (S179, H277, H189, and N199) were found for 1,5-bis[(E)-2-(3,4-dichlorophenyl)ethenyl]-2,4-dinitrobenzene that possessed inhibitory activity. In support of this notion, NSC26820 that had ortho-positioned COOH moieties completely lost the inhibitory effects (Table 3). In addition, NSC107408 showed no inhibition because it lacked the 1,3-dinitrobenzene moiety and was unable to form interactions with residues S197, H277, H189, and N199 of the AKG site (FIGS. 5A and 5B).

TABLE 3

Inhibition effects of selected hits on KDM4A and KDM4B.

| Compound ID | KDM | Demethylase[a] Residual Activity (%) | $IC_{50}$ (μM) | FDH[b] Residual Activity (%) | Compound structure | Ranking 4B |
|---|---|---|---|---|---|---|
| NSC636819 | 4A | 28 | 15.5 | >80 | 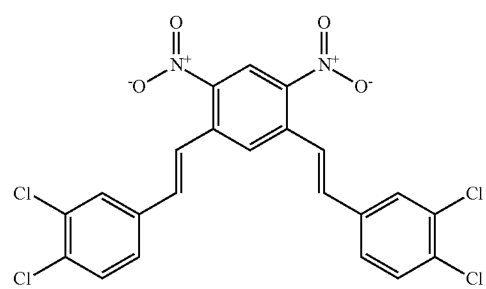 | 100 |
|  | 4B | 35 | 9.3 |  | | |
| NSC107408 | 4A | 99 | — | >80 | 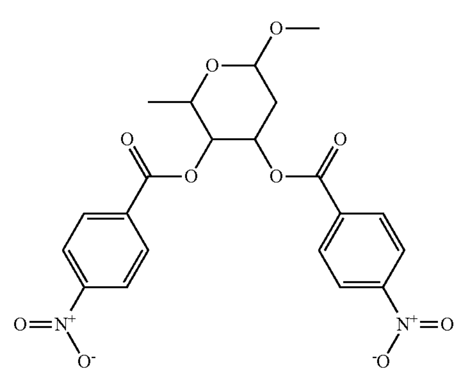 | 3 |
|  | 4B | 64 | — |  | | |

TABLE 3-continued

Inhibition effects of selected hits on KDM4A and KDM4B.

| Compound ID | KDM | Demethylase[a] Residual Activity (%) | IC$_{50}$ (µM) | FDH[b] Residual Activity (%) | Compound structure | Ranking 4B |
|---|---|---|---|---|---|---|
| NSC85021 | 4A | 82 | — | >80 | 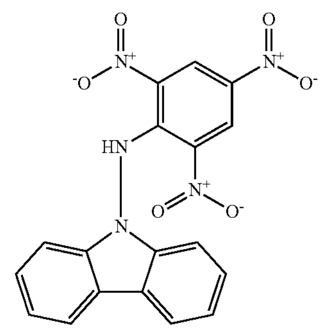 | 223 |
|  | 4B | 65 | — |  | | |
| NSC28620 | 4A | 111 | — | >80 | 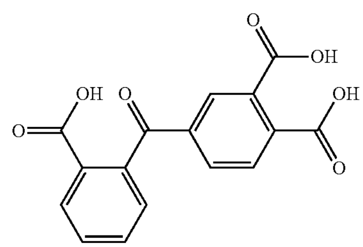 [SMILES: O=C(O)c1ccc(C(=O)c2ccccc2C(=O)O)cc1C(=O)O] | 271 |
|  | 4B | 110 | — |  | | |
| NSC15975 | 4A | 73 | — | >80 | 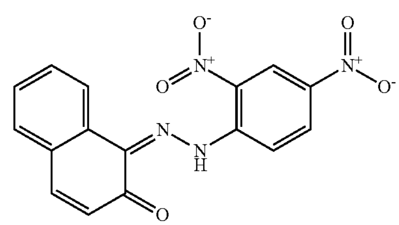 [SMILES: O=C1C=Cc2ccccc2/C1=N/Nc1ccc([N+](=O)[O-])cc1[N+](=O)[O-]] | 83 |
|  | 4B | 90 | — |  | | |
| NSC640999 | 4A | 77 | — | >80 | 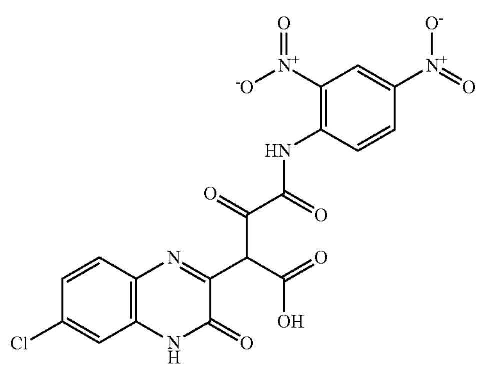 | 2 |
|  | 4B | 49 | — |  | | |
| NSC659196 | 4A | 92 | — | >80 | 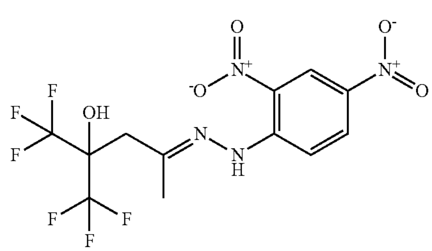 | 33 |
|  | 4B | 56 | — |  | | |

TABLE 3-continued

Inhibition effects of selected hits on KDM4A and KDM4B.

| Compound ID | KDM | Demethylase[a] Residual Activity (%) | IC$_{50}$ (μM) | FDH[b] Residual Activity (%) | Compound structure | Ranking 4B |
|---|---|---|---|---|---|---|
| NSC124029 | 4A | 93 | — | 97 | 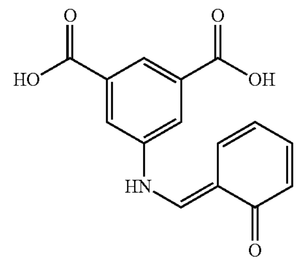 [SMILES: O=C1C=CC=C/C1=C\Nc1cc(C(=O)O)cc(C(=O)O)c1] | 159 |
| | 4B | 62 | — | — | | |
| NSC1018 | 4A | 85 | — | >80 | 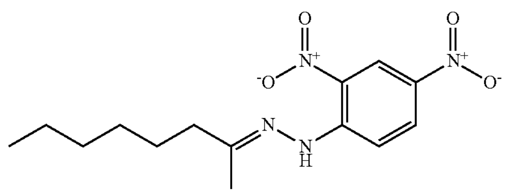 | 93 |
| | 4B | 62 | — | — | | |
| NSC6129 | 4A | 100 | — | >80 | 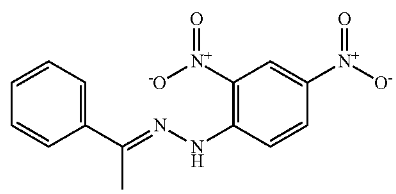 | 62 |
| | 4B | 52 | — | — | | |

Genetic and Pharmacological Inhibition of KDM4A and KDM4B Induced Apoptosis

Figure 6A:
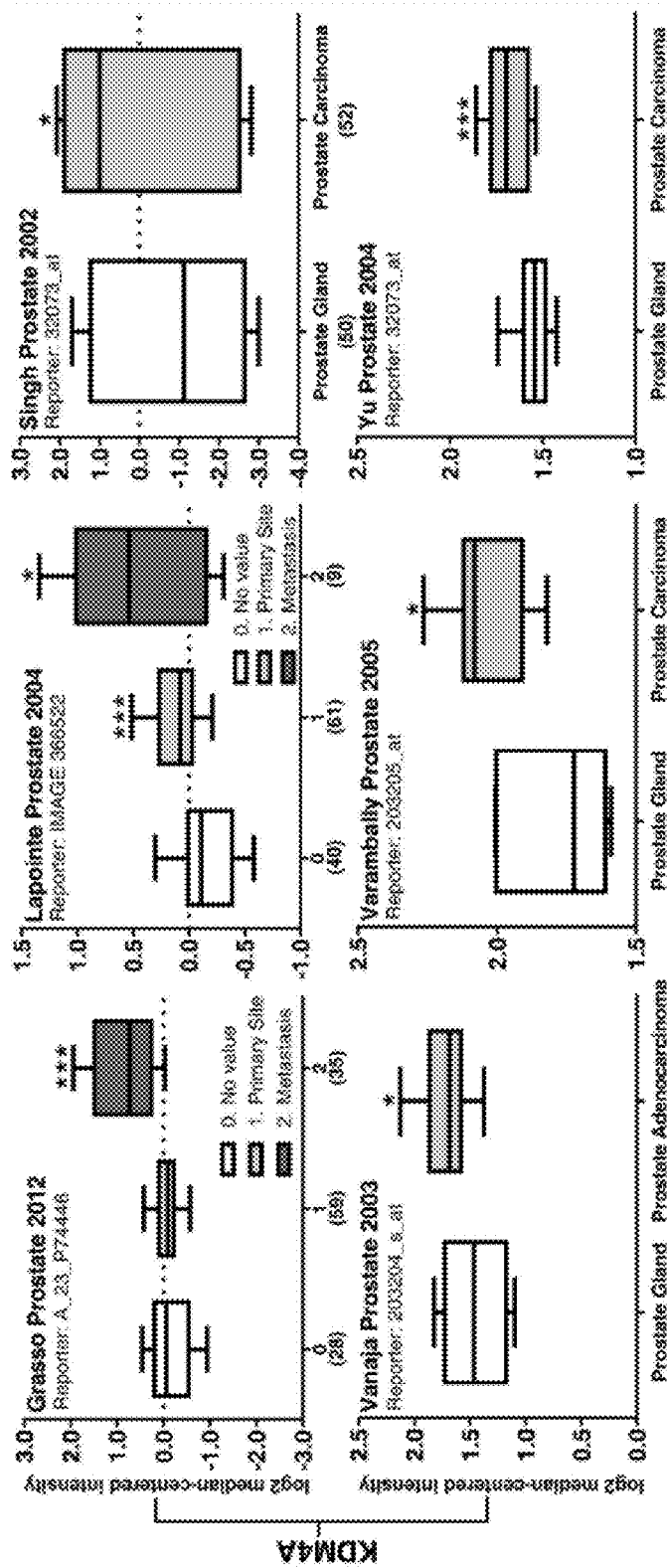
FIG. 6(A) shows the expression values of KDM4A in normal prostate gland and tumor tissues from the selected studies, which were obtained from Oncomine™ (Compendia Bioscience, Ann Arbor, Mich., USA) database. The box whisker plots show the box encompasses 25th-75th percentile, median as line within the box, and 10th and 90th percentiles as error bars.
Figure 6B:
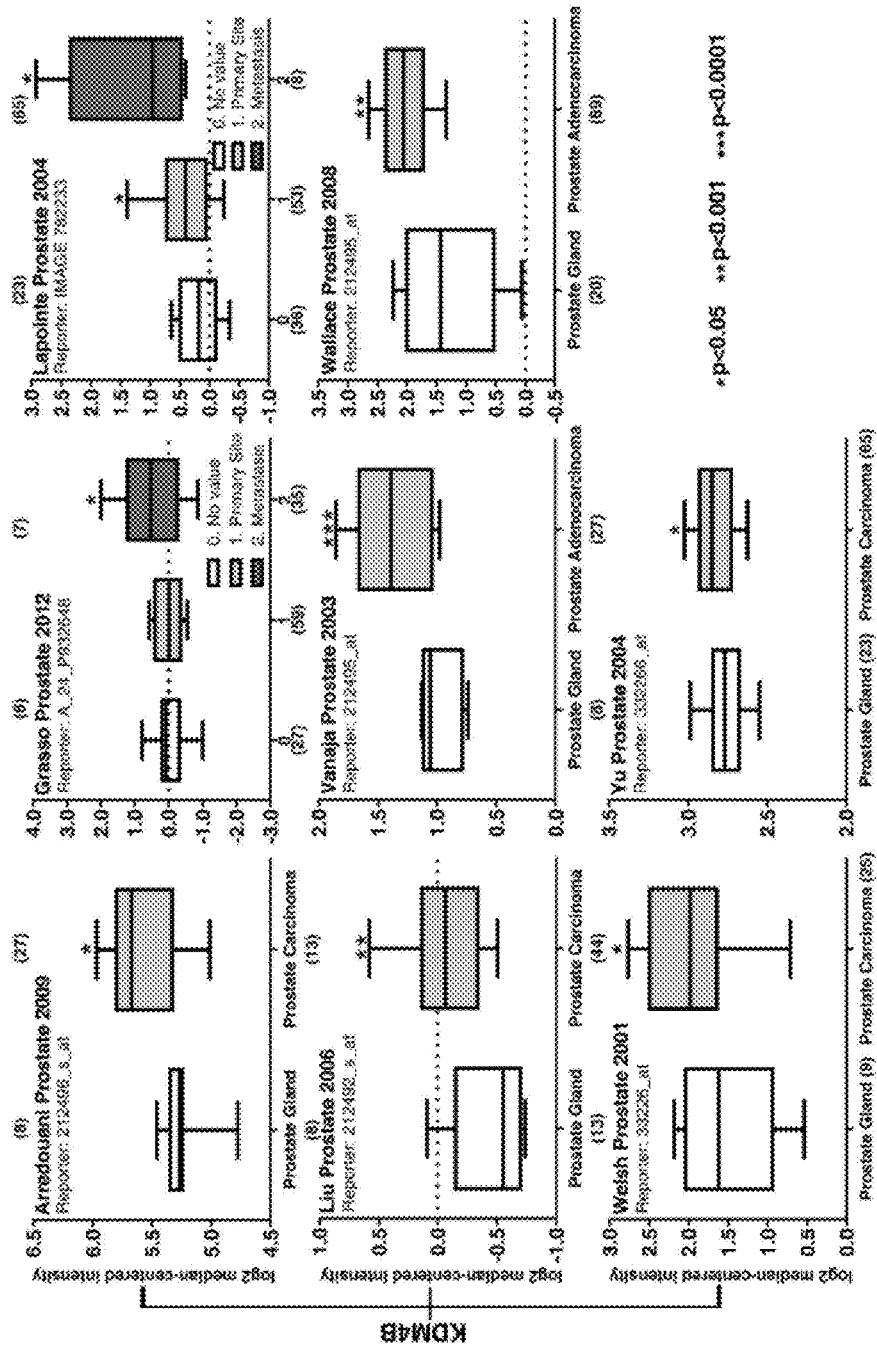
FIG. 6(B) shows the expression values of KDM4B in normal prostate gland and tumor tissues from the selected studies, which are obtained from Oncomine™ database. The box whisker plots show the box encompasses 25th-75th percentile, median as line within the box, and 10th and 90th percentiles as error bars. P values are determined by one-tailed Student's T-test and calculated based on the comparison of normal vs. cancer; normal vs. primary sites; or normal vs. metastasis.
Figure 13A:
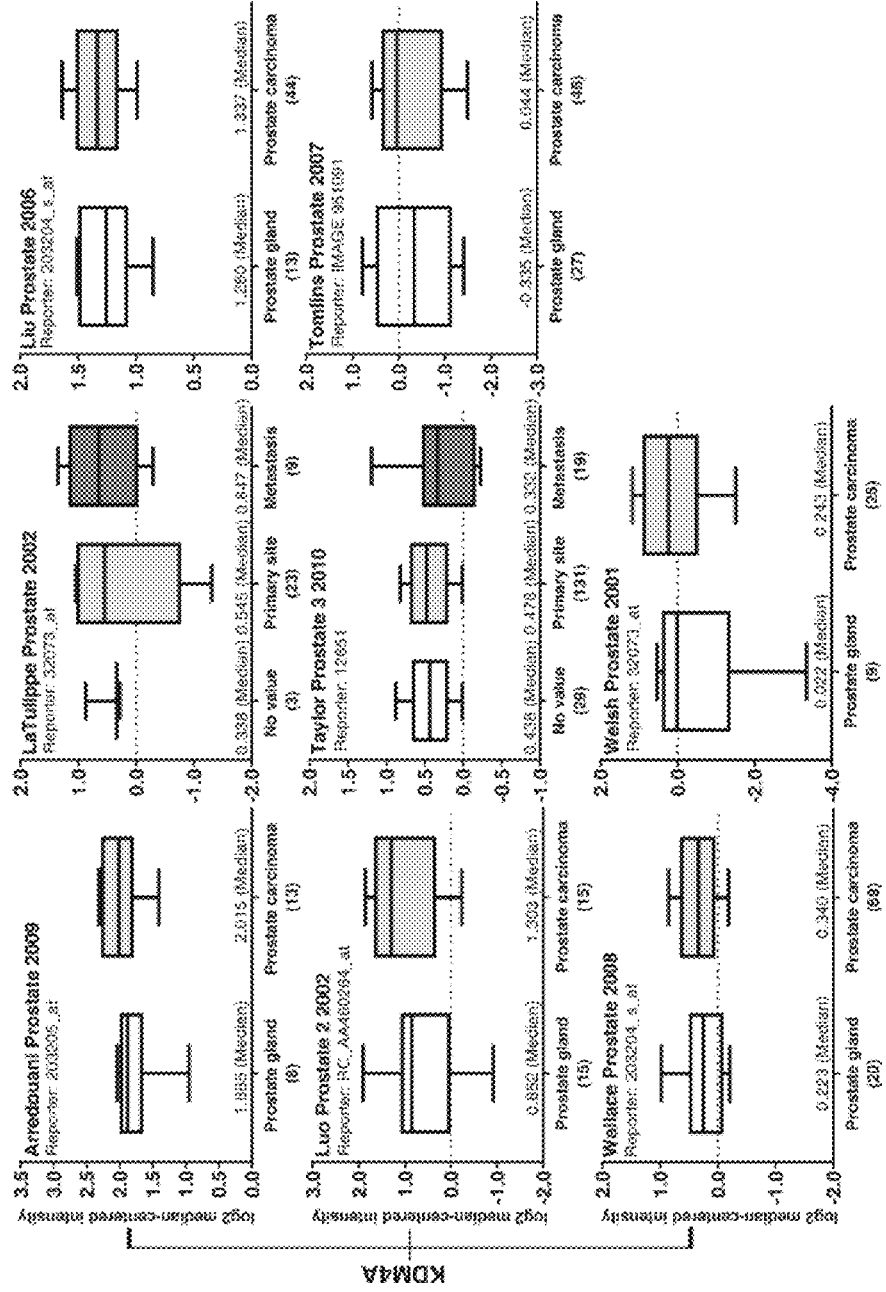
FIG. 13(A) shows that the rest of datasets exhibit higher median values of KDM4A expression in PCa sites, despite no statistical significance. The expression values of KDM4A and KDM4B in normal prostate gland and tumor tissues from the selected studies are obtained from Oncomine™ (Compendia Bioscience, Ann Arbor, Mich., USA) database. The box whisker plots show the box encompasses 25th-75th percentile, median as line within the box, and 10th and 90th percentiles as error bars.
Figure 13B:
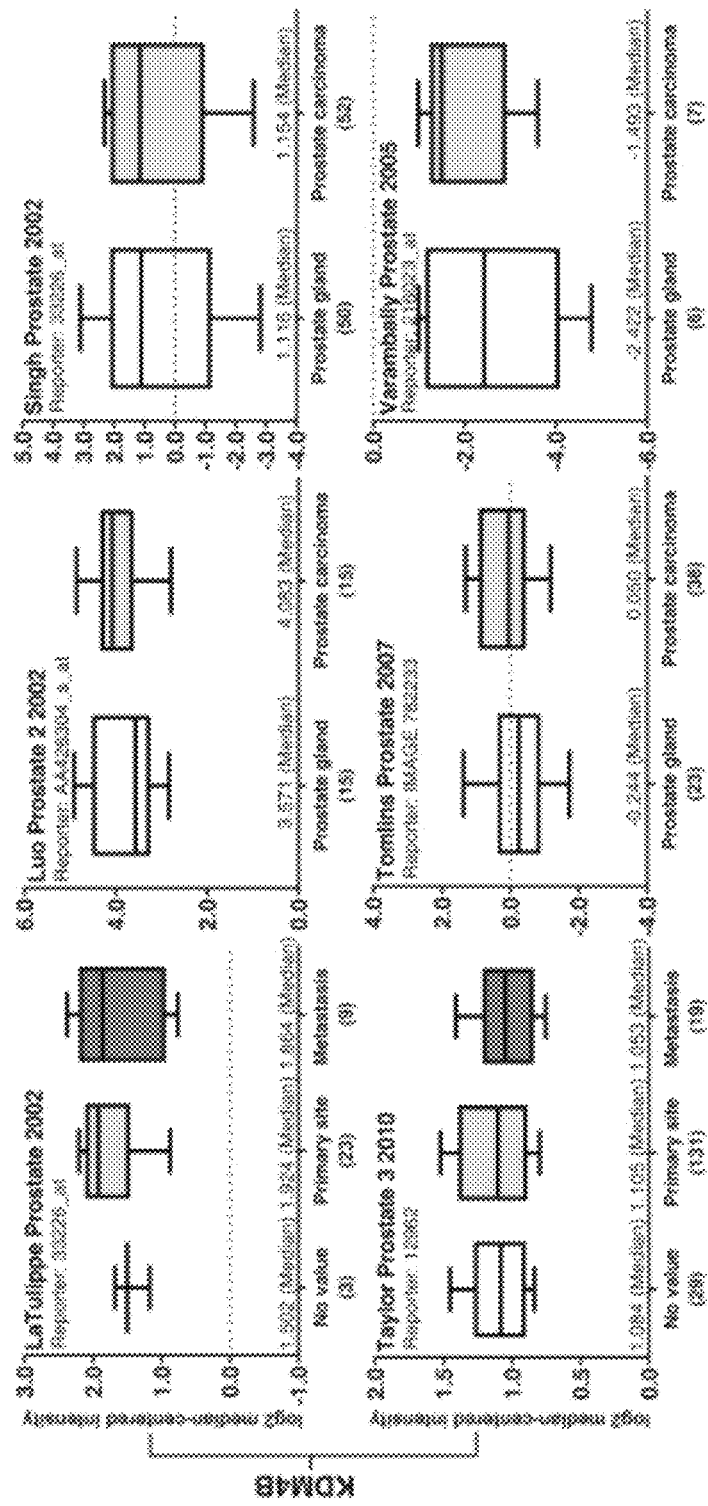
FIG. 13(B) shows that the rest of datasets exhibit higher median values of KDM4B expression in PCa sites, despite no statistical significance. The expression values of KDM4A and KDM4B in normal prostate gland and tumor tissues from the selected studies are obtained from Oncomine™ database. The box whisker plots show the box encompasses 25th-75th percentile, median as line within the box, and 10th and 90th percentiles as error bars. P values are determined by one-tailed Student's T-test and calculated based on the comparison of normal vs. cancer; normal vs. primary sites; or normal vs. metastasis.

Several studies have reported that KDM4 family members are over-expressed in various cancers. To further support clinical relevance of KDM4A and KDM4B in prostate cancer, the present invention took advantage of the comprehensive database collection on Oncomine™ (Compendia Bioscience, Ann Arbor, Mich., USA) database to examine their expression profile between normal prostate gland and tumor tissues. Among 14 datasets available, a statistically significant (p<0.05) elevation of KDM4A was seen for 6, and KDM4B for 8 in PCa compared to normal/benign samples (FIGS. 6A and 6B). The rest of datasets also exhibited higher median values of KDM4A/KDM4B expression in PCa sites, despite no statistical significance (FIGS. 13A and 13B). Strikingly, the level of KDM4A and B's expression was positively correlated with prostate cancer progression (normal, primary PCa, and metastatic PCa).

Figure 6C:
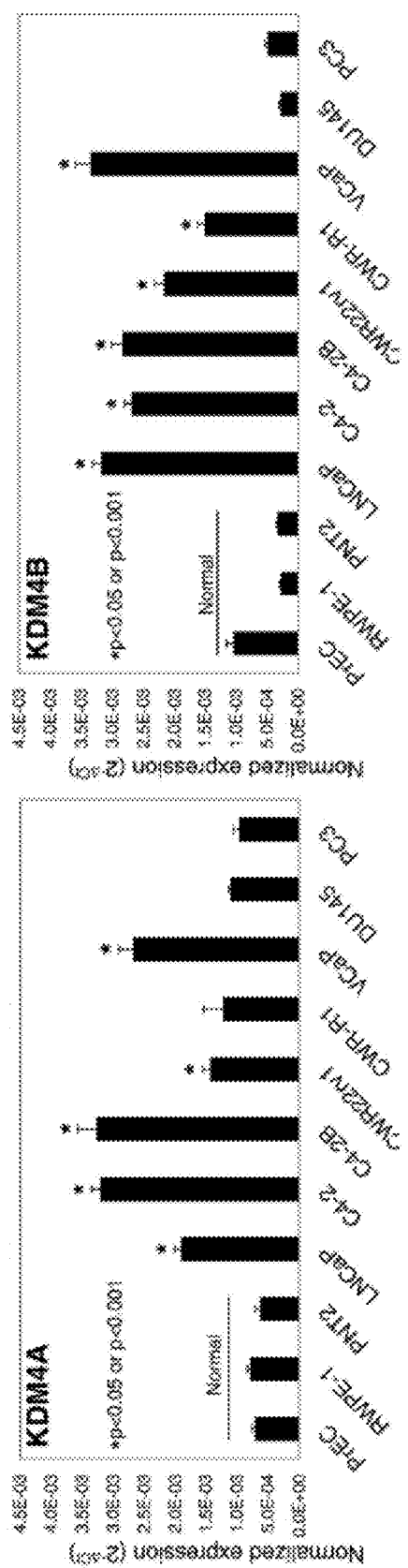
FIG. 6(C) shows the qRT-PCR analysis of KDM4A and KDM4B expression in normal prostate primary cell (PrEC), normal prostate epithelial cell lines (RWPE-1 and PNT2), and prostate cancer cell lines (LNCaP, C4-2, C4-2B, CWR22rv1, CWR-R1, VCaP, DU145 and PC3). Asterisks indicate significant overexpression as compared to normal cells.

The present invention also examined the expression of KDM4A and KDM4B in several laboratory-cultured prostate cancer cell models: normal prostate epithelial cells (PrEC, RWPE-1 and PNT2) and a number of prostate cancer cell lines (LNCaP, C4-2, C4-2B, CWR22rv1, CWR-R1, VCap, DU145 and PC3). Essentially all prostate cancer cells exhibited higher expression of KDM4A as compared with normal prostate epithelial cell lines, in which statistical significance was found for LNCaP, C4-2, C4-2B, CWR22rv1, and VCap cells (FIG. 6C). Similarly, with the exception of DU145 and PC3, KDM4B was over-expressed in all other malignant cell lines.

Figure 7A:
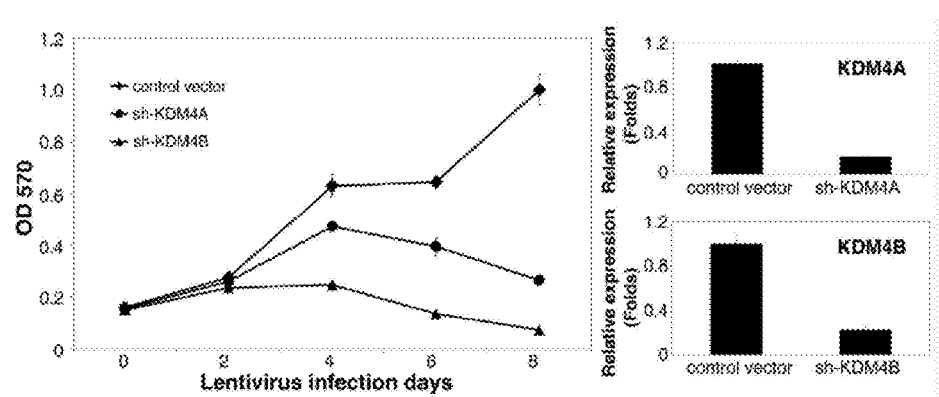
FIG. 7(A) shows KDM4A and KDM4B are crucial for growth of LNCaP cells. LNCaP cells are infected with lentivirus with control shRNA (control) and shKDM4A or shKDM4B as indicated (left panel). The qRT-PCR analysis is performed to evaluate the expression of KDM4s (right panel).

To assess whether KDM4A or KDM4B was crucial for prostate cancer cell growth, LNCaP cells were treated with shKDM4A or shKDM4B to knockdown the expression of KDM4A or KDM4B (FIG. 7A). A significantly reduced level of cell growth was found in KDM4A and KDM4B knockdown cells (FIG. 7A), indicating that these two molecules were critical to the viability of the cancer cells and thus were potentially useful targets for intervention.

Figure 7B:
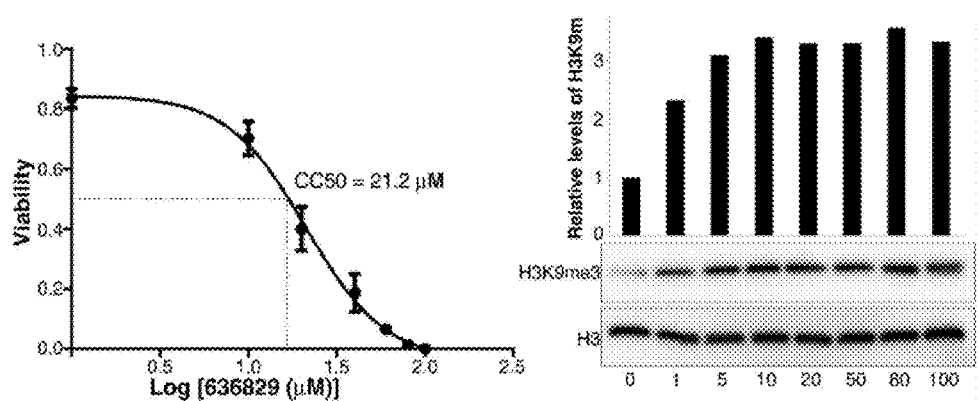
FIG. 7(B) shows cytotoxicity IC50 (CC50) and inhibition of H3K9me3 by 1,5-bis[(E)-2-(3,4-dichlorophenyl)ethenyl]-2,4-dinitrobenzene in LNCaP cells. LNCaP cells are treated with 1,5-bis[(E)-2-(3,4-dichlorophenyl)ethenyl]-2,4-dinitrobenzene for three days, and the viability is measured by viable cell count. SD is derived from biological triplicates. The level of H3K9me3 of 1,5-bis[(E)-2-(3,4-dichlorophenyl)ethenyl]-2,4-dinitrobenzene-treated cells (24 hr) is detected and quantified by AlphaView SA (Cell Biosciences Inc.). The level of H3K9me3 is shown by bar graph.
Figure 7C:
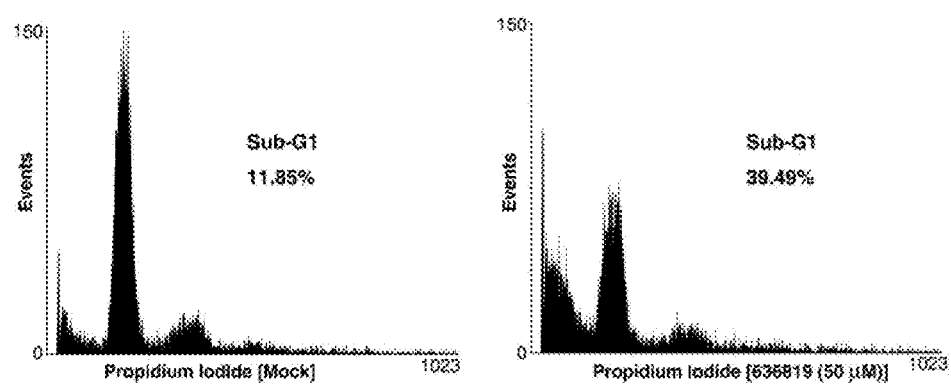
FIG. 7(C) shows flow cytometric analysis of DNA contents in LNCaP cells treated with DMSO (mock) or 50 µM 1,5-bis[(E)-2-(3,4-dichlorophenyl)ethenyl]-2,4-dinitrobenzene for 3 days.

Due to the shKDM4A and 4B knockdown data whether 1,5-bis[(E)-2-(3,4-dichlorophenyl)ethenyl]-2,4-dinitrobenzene, which inhibited both KDM4A and 4B would similarly reduce the viability of LNCaP was tested. As shown in FIG. 7B, this compound effectively killed LNCaP cells with a cytotoxicity IC50 of 21.2 μM. Cell flow cytometric analysis showed that there were nearly four-fold apoptotic LNCaP cells produced upon 1,5-bis[(E)-2-(3,4-dichlorophenyl)ethenyl]-2,4-dinitrobenzene treatment as compared to mock cells (11.9% vs. 39.5%) (FIG. 7C). To validate the effect of 1,5-bis[(E)-2-(3,4-dichlorophenyl)ethenyl]-2,4-dinitrobenzene, the present invention examined the cellular level of H3K9me3 of the treated cells. As shown in FIG. 7B, 1,5-bis[(E)-2-(3,4-dichlorophenyl)ethenyl]-2,4-dinitrobenzene-treated cells had a notable increase in the level of H3K9me3 in a dose-dependent manner; 5 μM of 1,5-bis[(E)-2-(3,4-dichlorophenyl)ethenyl]-2,4-dinitrobenzene treatment essentially completely blocked the demethylating activity toward H3K9me3. These results collectively suggested that inhibition of KDM4A/KDM4B by shRNA or by 1,5-bis[(E)-2-(3,4-dichlorophenyl)ethenyl]-2,4-dinitrobenzene specifically inhibited the demethylating activity of H3K9me3 and strongly blocked cell growth. As a comparison, the present invention utilized the dimethyl ester form of PD2, the most potent inhibitor against KDM4E (in vitro assay), allowing to penetrate into the cells. Consistent with their results, a high CC50 value was found in LNCaP cells (588.7 μM).

Figure 8A:
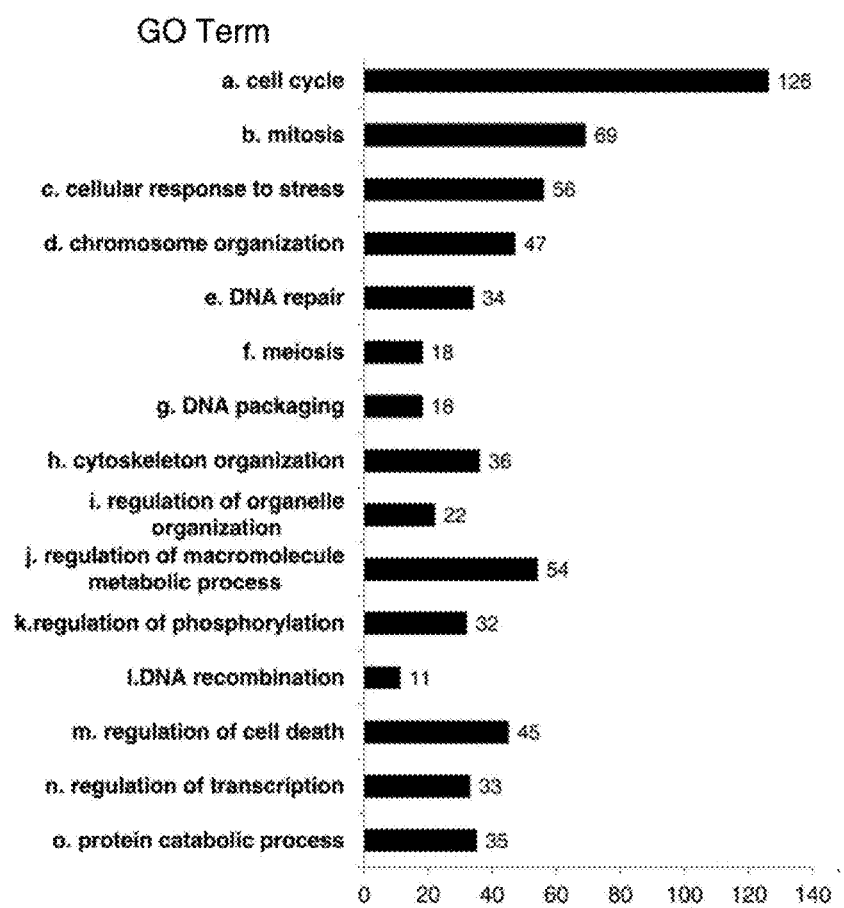
FIG. 8(A) shows DAVID functional annotation of the genes that shows two-folds alterations in expression. GO terms associated with the altered genes that show statistically strong enrichment with low P-values are listed. Bar graph and the numbers labelled indicate gene count of each pathway. % of hits indicates the percentage of genes that are altered in each GO.

Inhibition of KDM4 by 1,5-bis[(E)-2-(3,4-dichlorophenyl)ethenyl]-2,4-dinitrobenzene Negatively Regulateed AR Responsive Genes To understand the mechanisms associated with growth inhibition and apoptosis induction by 1,5-bis[(E)-2-(3,4-dichlorophenyl)ethenyl]-2,4-dinitrobenzene, the present invention characterized the differential gene expression profiles in LNCaP cells treated with or without 1,5-bis[(E)-2-(3,4-dichlorophenyl)ethenyl]-2,4-dinitrobenzene using microarray analysis (≥two-fold alterations). As shown in FIG. 8A, functional annotations indicated a number of differentially expressed genes related to cell division and DNA processes (Bar graph and the numbers labeled indicate gene count of each pathway). GO terms associated with the altered genes that showed statistically strong enrichment with low P-values were listed. % of hits indicated the percentage of genes that were altered in each GO (Table 4).

TABLE 4

The data of the GO term

| Index | P-Value | Total genes in each GO term | % of hits |
|---|---|---|---|
| a | 2.32E−48 | 776 | 16 |
| b | 8.58E−45 | 220 | 31 |
| c | 2.65E−11 | 566 | 10 |
| d | 2.71E−09 | 485 | 10 |
| e | 3.91E−09 | 284 | 12 |
| f | 8.23E−08 | 98 | 18 |
| g | 1.13E−06 | 117 | 15 |
| h | 1.07E−05 | 436 | 8 |
| i | 4.63E−05 | 217 | 10 |
| j | 1.10E−04 | 857 | 6 |
| k | 9.51E−04 | 466 | 6 |
| l | 5.00E−03 | 105 | 10 |
| m | 5.90E−03 | 815 | 6 |
| n | 9.09E−03 | 564 | 6 |
| o | 1.23E−02 | 622 | 6 |

Figure 8B:
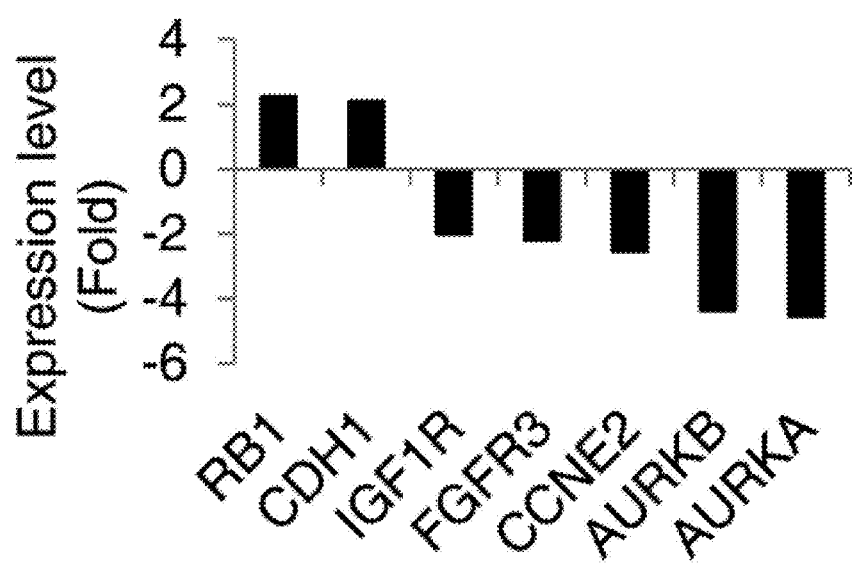
FIG. 8(B) shows expression of tumour suppressors and oncogenes that are up- and down-regulated in the inhibitor treated cell, respectively.
Figure 8C:
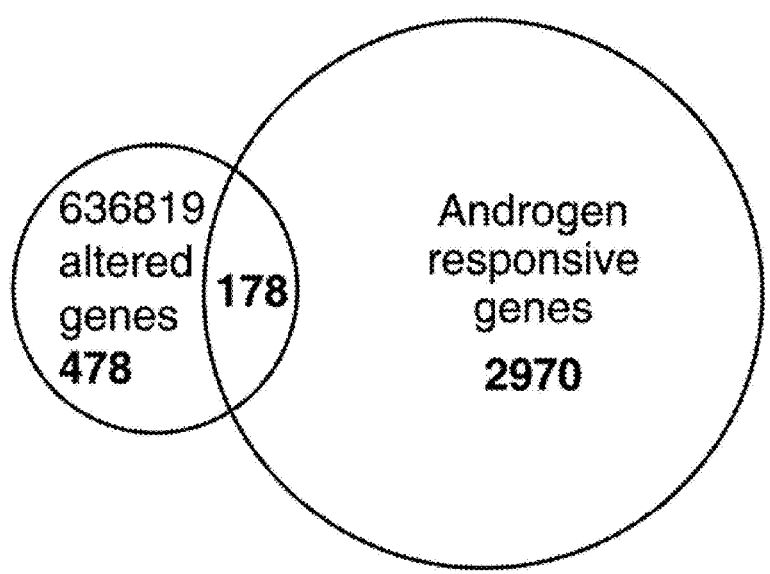
FIG. 8(C) shows overlap of the inhibitor-altered genes with androgen responsive genes.
Figure 9:
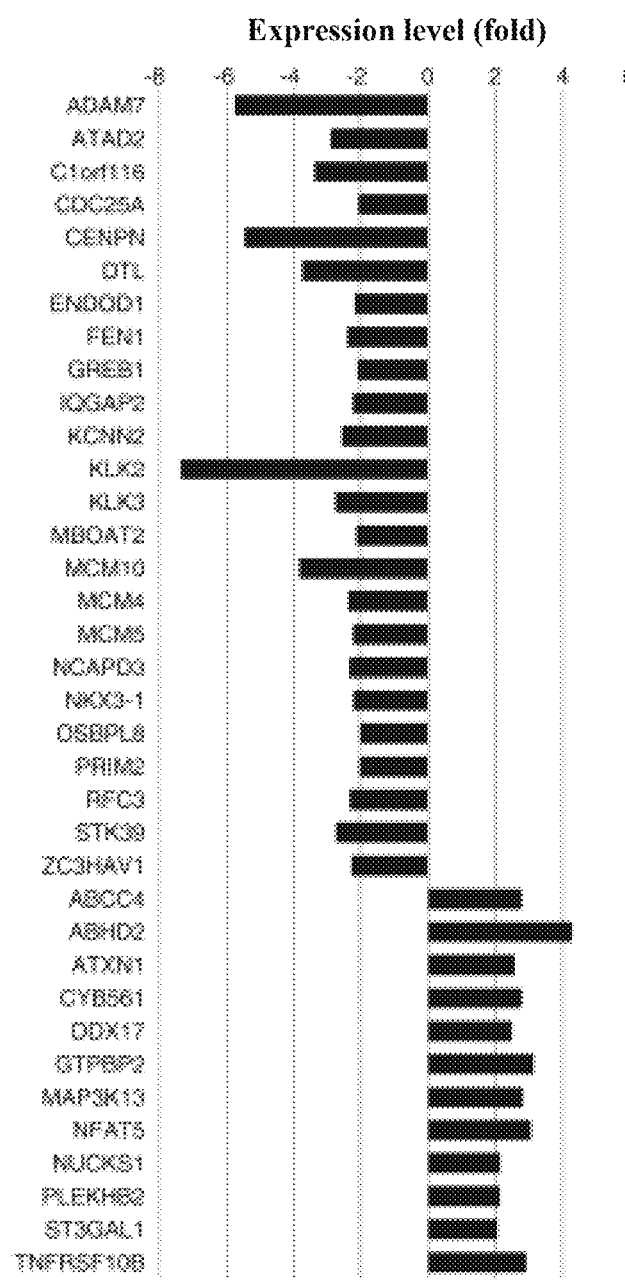
FIG. 9 shows AR-signature genes are differentially expressed in 1,5-bis[(E)-2-(3,4-dichlorophenyl)ethenyl]-2,4-dinitrobenzene-treated LNCaP cell.

Most intriguingly, a significant portion (27%=178/656) of the altered genes were found to be androgen responsive genes (FIG. 8C). The mRNA expression of AR signature genes was validated using qRT-PCR (FIG. 9). This is consistent with the previous results that both KDM4A and KDM4B (as well as KDM4C) are coactivators of AR. In addition to the alteration of androgen responsive genes, 1,5-bis[(E)-2-(3,4-dichlorophenyl)ethenyl]-2,4-dinitrobenzene induced up-regulation of tumour suppressors RB1, CDH1; as well as down-regulation of oncogenes IGF1R, FGFR3, CCNE2, AURKA and AURKB (FIG. 8B) which might contribute to the loss of proliferating and survival advantages for the tumour cell. Thus, 1,5-bis[(E)-2-(3,4-dichlorophenyl)ethenyl]-2,4-dinitrobenzene specifically inhibited the expression of genes involved in DNA-dependent processes, cell proliferation and AR-dependent signaling in prostate cancer cells. Given the importance of AR in prostate carcinogenesis, compounds inhibited KDM4A and 4B could be beneficially used to overcome castration-resistance.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating cancer in a subject in need thereof, which comprises administering an effective amount of a compound and a pharmaceutically acceptable carrier to the subject, wherein the compound has a structure of a formula I:

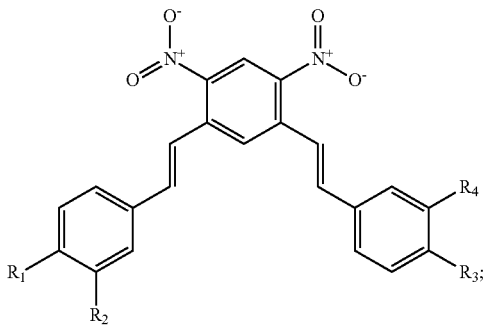

wherein $R_1$, $R_2$, $R_3$ and $R_4$ are independently F, Cl, Br, or I.

2. The method of claim 1, wherein the cancer is a prostate cancer, a breast cancer, a colorectal cancer, a lung cancer, a gastric cancer, an esophageal cancer, a lymphoma, a renal cancer and or a medulloblastoma.

3. The method of claim 2, wherein the cancer is the prostate cancer.

4. The method of claim 1, wherein the compound is a 1,5-bis[(E)-2-(3,4-dichlorophenyl)ethenyl]-2,4-dinitrobenzene.

5. The method of claim 1, wherein the compound inhibits an expression of a histone lysine demethylase (KDM) in the subject.

6. The method of claim 5, wherein the compound inhibits a cancer cell growth or induce an apoptosis of a cancer cell by inhibiting the expression of the KDM in the subject.

7. The method of claim 5, wherein the KDM is a KDM4A or a KDM4B.

8. The method of claim 5, wherein the inhibiting the expression of the KDM comprises inhibiting a demthylating function of the KDM.

9. The method of claim 8, wherein the KDM demethylates a histone.

10. The method of claim 9, wherein the histone is a H3K9me3, a H3K9me2, a H3K36me3, or a H3K36me2.

11. The method of claim 10, wherein the histone is the H3K9me3 or the H3K9me2.

* * * * *